(12) United States Patent
Gordon et al.

(10) Patent No.: US 8,796,483 B2
(45) Date of Patent: Aug. 5, 2014

(54) CYCLIC METAL AMIDES AND VAPOR DEPOSITION USING THEM

(75) Inventors: Roy G. Gordon, Cambridge, MA (US); Adam S. Hock, Boston, MA (US); Jaeyeong Heo, Somerville, MA (US); Prasert Sinsermsuksakul, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 511 days.

(21) Appl. No.: 13/077,241

(22) Filed: Mar. 31, 2011

(65) Prior Publication Data

US 2012/0027937 A1 Feb. 2, 2012

Related U.S. Application Data

(60) Provisional application No. 61/320,069, filed on Apr. 1, 2010.

(51) Int. Cl.
*C07F 7/22* (2006.01)
*C07F 7/24* (2006.01)
*C23C 16/00* (2006.01)

(52) U.S. Cl.
USPC .......................................................... 556/81

(58) Field of Classification Search
USPC ..................................... 556/9, 81; 427/248.1
See application file for complete search history.

(56) References Cited

U.S. PATENT DOCUMENTS

| 7,557,229 B2 | 7/2009 | Gordon et al. |
| 2008/0118636 A1 | 5/2008 | Shin et al. |
| 2009/0124039 A1 | 5/2009 | Roeder et al. |
| 2009/0212280 A1 | 8/2009 | Werner et al. |
| 2009/0305458 A1 | 12/2009 | Hunks et al. |

FOREIGN PATENT DOCUMENTS

EP 1698614 A1 9/2006

OTHER PUBLICATIONS

Mansell et al., Inorganic Chemistry, vol. 50, pp. 2252-2263 (2011).*
Zabula et al., Organometallics, vol. 27, No. 12, pp. 2756-2760 (2008).*
Michael Veith, Angewandte Chemie International Edition in English, vol. 26, No. 1, pp. 1-92 (1987).*
Wolfgang A. Herrmann, Angewandte Chemie International Edition, vol. 41, pp. 1290-1309 (2002).*

(Continued)

*Primary Examiner* — Porfirio Nazario Gonzalez
(74) *Attorney, Agent, or Firm* — Wilmer Cutler Pickering Hale and Dorr LLP

(57) ABSTRACT

Novel cyclic amides containing tin or lead are disclosed. These cyclic amides can be used for atomic layer deposition or chemical vapor deposition of tin or lead as well as their oxides, sulfides, selenides, nitrides, phosphides, carbides, silicides or borides or other compounds. Tin(IV) oxide, $SnO_2$, films were deposited by reaction of a cyclic tin amide vapor and $H_2O_2$ or $NO_2$ as oxygen sources. The films have high purity, smoothness, transparency, electrical conductivity, density, and uniform thickness even inside very narrow holes or trenches. Deposition temperatures are low enough for thermally sensitive substrates such as plastics. Suitable applications of these films include displays, light-emitting diodes, solar cells and gas sensors. Doping $SnO_2$ with aluminum was used to reduce its conductivity, making material suitable as the active semiconductor layer in electron multipliers or transparent transistors. Deposition using the same tin precursor and $H_2S$ deposited tin monosulfide, SnS, a material suitable for solar cells.

22 Claims, 21 Drawing Sheets

(56) References Cited

OTHER PUBLICATIONS

Barone, Giampaolo et al. "Synthesis and Thermal Decomposition Studies of *Homo-* and Heteroleptic Tin (IV) Thiolates and Dithiocarbamates: Molecular Precursors for Tin Sulfides." J. Chem. Soc., Dalton Trans., The Royal Society of Chemistry., Feb. 18, 2002, pp. 1085-1092.

Drozd, V.E. et al. "Synthesis of Conducting Oxides by ML-ALE." Applied Surface Science., Elsevier. Jul. 1994. pp. 591-594.

Du, X. et al. "In Situ Examination of Tin Oxide Atomic Layer Deposition Using Quartz Crystal Microbalance and Fourier Transform Infrared Techniques." J. Vac Sci. Technol., American Vacuum Society. Jun. 7, 2005, (23)4, pp. 581-588.

Du, X. et al. "Thickness Dependence of Sensor Response for CO Gas Sensing by Tin Oxide Films Grown Using Atomic Layer Deposition." Sensors and Actuators B: Chemical., Elsevier B.V., Aug. 2008, 135, pp. 152-160.

Elam, Jeffrey W. et al. "Atomic Layer Deposition of Tin Oxide Films Using Tetrakis (dimethylamino) Tin." J. Vac. Sci. Technol., American Vacuum Society., Jan. 29, 2008, 26(2), pp. 244-252.

Heo, Jaeyeong et al. "(Sn,Al)Ox Films Grown by Atomic Later Deposition." The Journal of Physical Chemistry., ACS Publications., American Chemical Society., Apr. 28, 2011, 115, pp. 10277-10283.

Herrmann, Wolfgang A. et al. "Stable Cyclic Germanediyls ("Cyclogermylenes"): Synthesis, Structure, Metal Complexes, and Thermolyses." Angew. Chem. Int. Engl., VCH Verlagsgesellschaft mbH. Aug. 1992, pp. 1485-1488.

International Search Report and Written Opinion issued in International Application PCT/US2011/030771, mailed Jul. 25, 2011, 11 pages.

Kim, Jay Yu et al. "Tin Monosulfide Thin Films Grown by Atomic Later Deposition Using Tin 2,4-Pentanedionate and Hydrogen Sulfide." J. Phys. Chem., American Chemical Society. Aug. 2010, vol. 114, No. 41, pp. 17597-17603.

Lehmann, John F. et al. "Core Excitation Spectroscopy of Stable Cyclic Diaminocarbenes, -silylenes, and -germylenes." Organometallics., American Chemical Society. Apr. 14, 1999, vol. 18, pp. 1862-1872.

Mansell, Stephen M. et al. "Coordination Chemistry of N-Heterocyclic Stannylenes: A Combined Synthetic and Mossbauer Spectroscopy Study", Inorganic Chemistry, Mar. 21, 2011, 50(6):2252-2263.

Mansell, Stephen M. et al. "Synthesis and Structural Characterization of Tin Analogues of *N*-Heterocyclic Carbenes." Inorganic Chemistry. American Chemical Society. Aug. 2008, vol. 47, No. 23, pp. 11367-11375.

Meller, Anton et al. "Synthese and Isolierung Neuer Germanium (II)-Verbindungen Und Freier Germylene." Chem. Ber. May 1984, 118, pp. 2020-2029 (Abstract in English).

Schafer, Annemarie et al. "Aminosilylgermylenes: (*E*)-Digermene Versus Germylene Crystallization." Z. Anorg. Allg. Chem., Wiley-VCH GmbH. Feb. 1998, 624, pp. 1405-1408.

Sundqvist, Jonas et al. "Growth of SnO2 Thin Films by Atomic Layer Deposition and Chemical Vapour Deposition: A Comparative Study." Thin Solid Films. Mar. 2006, vol. 514, pp. 63-68.

Tarre, A. et al. "New Routes to SnO2 Heteroepitaxy." Vacuum, Elsevier Science Ltd. No Month Listed. 2002, vol. 67, pp. 571-575.

Teff, D.J. et al. "Synthesis and Thermolytic Behavior of Mixed-Valence Homo- and Heterometallic Group 14 Alkoxides." Inorg Chem., American Chemical Society., Apr. 29, 1998, vol. 37, pp. 2547-2553.

Tomasik, Adam C. et al. "Synthesis and Characterization of Three New Thermally Stable N-heterocyclic Germylenes." Journal of Organometallic Chemistry. Elsevier B.V. Dec. 2008, vol. 694, pp. 2122-2125.

Utriainen, M. et al. "Atomic Force Microscopy Studies of SnO2 Thin Film Microstructures Deposited by Atomic Layer Epitaxy." Mikrochimica Acta., Springer Verlag, Austria. No Month Listed. 2000, vol. 133, pp. 119-123.

Utriainen, M. et al. "Controlled Electrical Conductivity in SnO2 Thin Films by Oxygen or Hydrocarbon Assisted Atomic Layer Expitaxy." Journal of the Electrochemical Society., The Electrochemical Society, Inc. No Month Listed. 1999, 146(1), pp. 189-193.

Veith, Michael et al. "Synthese Und Charakterisierung der Siloxialane [H2AlOSiMe3]n Und [HAl(OtBu)(OSiMe3)]2 Sowie Redoxreaktionen von [H2AlOSiMe3]n Und [H2AlOtBu]2 Mit Einem Zinn(II)-Amid." Z. Anorg. Allg. Chem., vol. 628, Wiley-VCH Verlag GmbH., May 14, 2001, pp. 138-146. (Abstract in English).

Viirola, H. et al. "Controlled Growth of Antimony-doped Tin Dioxide Thin Films by Atomic Layer Epitaxy." Thin Solid Films., Elsevier B.V., May 1994, vol. 251, pp. 127-135.

Viirola, H. et al. "Controlled Growth of Tin Dioxide Thin Films by Atomic Layer Epitaxy.", Presented in Part at the 2nd International Symposium on Atomic Layer Epitaxy in Raleigh, NC, Jun. 2-5, 1992. Thin Solid Films., Elsevier Science S.A., Mar. 1994, vol. 249, pp. 144-149.

\* cited by examiner

CYCLIC METAL AMIDES AND VAPOR DEPOSITION USING THEM

CROSS-REFERENCE TO RELATED APPLICATION

The present disclosure claims the benefit of the earlier filing date of U.S. Patent Application No. 61/320,069, filed on Apr. 1, 2010, the contents of which is incorporated by reference herein in its entirety.

FIELD OF THE INVENTION

This present disclosure relates to materials and processes for deposition of films containing metals on solid substrates, and in particular, to films comprising tin or lead or their oxides, sulfides or nitrides. This present disclosure may be applied to the fabrication of solar cells, displays, microelectronics devices, electron multipliers and gas sensors.

DESCRIPTION OF THE RELATED ART

Tin oxide ($SnO_2$) has attracted great attention over the last decades because of its high transparency and conductivity combined with superior stability. It is a natural n-type semiconductor due to oxygen vacancies with band gap ($E_g$) of ~3.62 eV. The dramatic change in conductivity due to charge exchange with absorbed gas species has extended its applications to gas sensors for the detection of carbon monoxide or hydrogen. Aluminum-doped tin oxide has been reported to be a useful active channel material of thin film transistors in organic light emitting diodes or flexible displays. One dimensional forms of nanowires or nanorods of $SnO_2$ were also reported to be grown by employing vapor-liquid-solid or aqueous growth techniques, which show strong emission of ultraviolet photoluminescence.

Meanwhile, there are several ways to fabricate $SnO_2$ thin films, such as sol-gel method, spray pyrolysis, electron-beam plasma-deposition, sputtering, chemical vapor deposition (CVD), plasma-induced CVD, and atomic layer deposition (ALD). Among them, ALD is one of the most promising that allows obtaining highly conformal materials, thanks to self-limiting layer-by-layer build-up of material. ALD has been known for its excellent thickness and composition controllability as well as resulting pin-hole free films of high density.

The demand for establishing low temperature ALD process is high especially for the area of thermally sensitive substrate materials such as plastics, organic light emitting diodes and photovoltaic cells. One important requirement for achieving ALD at low temperature is to find a volatile precursor with appropriate reactivity that leads to clean reactions with the counterpart reactant gas at low growth temperatures. ALD-growth of $SnO_2$ using $SnCl_4$ and water has been reported at 500° C. The deposited film was polycrystalline, but the growth temperature of 500° C. is so high that it cannot be deposited on plastic or exploited in organic light emitting diodes or flexible displays. Alkyltin compounds such as tetramethyltin, $Me_4Sn$, and tetraethyltin, $Et_4Sn$, with dinitrogen tetroxide, $N_2O_4$, as oxidant gas forms $SnO_x$ thin film in the temperature range of 250-450° C., which is still a temperature region too high for many substrates, such as plastics. Using two different precursor combinations of $SnCl_4/H_2O_2$ (hydrogen peroxide) and $SnI_4/O_2$, the maximum growth rate was obtained from 250-400° C. and 500-750° C. for each selection, respectively. Reaction of $SnCl_4$ and $H_2O_2$ produced $SnO_2$ films for possible applications as CO gas sensors. Still, these ALD reactions can contaminate the films with chloride impurities and corrode deposition equipment as well as requiring high growth temperatures. A non-halogenated Sn precursor, tetrakis(dimethylamino)tin, and $H_2O_2$ as oxidant gas produced $SnO_x$ at deposition temperatures of 50-300° C. However, this $SnO_x$ required further high temperature annealing to oxidize and crystallize the amorphous film and the film had relatively low density and refractive index as the growth temperature decreased below 200° C. Plasma-enhanced ALD using dibutyl tin diacetate and $O_2$ deposits $SnO_2$ at 200-400° C. This process requires complex plasma generating systems and cannot produce uniform films inside structures with high aspect ratios.

Other tin compounds, such as tin sulfide and tin nitride can also be useful. Tin sulfide can be used a component of thin-film solar cells, or thin-film transistors. Previously known methods for CVD of tin sulfide have required high substrate temperatures. A previously known method for ALD of SnS used a precursor containing oxygen that can produce oxygen contamination in the deposited SnS. Tin nitride can be thermally decomposed by laser heating for optical recording.

Lead compounds can be components of photo-detectors or of piezo-electric devices.

SUMMARY

One aspect of the present disclosure includes a process for depositing films comprising tin or lead. The films have uniform, conformal thicknesses and smooth surfaces.

An advantage of this process is its ability to form coatings with extremely uniform thickness.

A related aspect of the present disclosure is the deposition of coatings under conditions that produce good adhesion between substrates and the deposited coating.

An advantage of the process is that it permits deposition of tin oxide coatings with extremely smooth surfaces.

An additional advantage of the process is the vapor deposition of highly uniform coatings over a range of conditions such as concentrations of reactants and position of the substrate inside the reactor.

Another advantage of the present disclosure is its ability to make conformal coatings of over substrates with narrow holes, trenches or other structures. This ability is commonly known as "good step coverage."

Another aspect of the present disclosure is the preparation of coatings that are substantially free of pin-holes or other mechanical defects.

Another advantage of the present disclosure is the ability to deposit coatings with high electrical conductivity.

Another advantage of the present disclosure is the ability to deposit metal-containing coatings that adhere strongly to oxide substrates.

Another advantage of the present disclosure includes the ability to coat substrates with coatings at relatively low temperatures.

A further aspect of the present disclosure includes a process for atomic layer deposition of coatings without plasma damage to substrates.

Yet another aspect of the present disclosure includes a process for depositing electrically conductive tin oxide coatings.

Another particular aspect of the present disclosure includes a process for depositing tin or lead sulfide coatings having useful semiconductor properties.

An additional aspect of the present disclosure is the deposition of tin sulfide or tin oxide layers in a solar cell.

A further aspect of the present disclosure includes a process for depositing tin oxide-magnesium oxide laminates having useful properties for micro-channel plate electron multipliers.

In one aspect of the present disclosure, vapors of a volatile tin cyclic amide compound are reacted with hydrogen sulfide gas at a surface to produce thin layers of tin sulfide on the surface.

In another aspect of the present disclosure, vapors of a volatile cyclic tin amide with an oxygen-containing gas or vapor to form tin oxide. Suitable oxygen containing compounds include oxygen, ozone, water vapor and hydrogen peroxide.

In other embodiments of the present disclosure, metal, metal oxide, metal sulfide, metal nitride, metal selenide, metal phosphide, metal carbide, metal silicide, or metal boride films are deposited.

In some embodiments, a reaction may be carried out in a manner to form films on substrates that may include holes or trenches. Coatings may also be placed on powders, wires or around and within complicated mechanical structures.

BRIEF DESCRIPTION OF THE DRAWINGS

The foregoing and various other aspects, features, and advantages of the present disclosure may be more fully appreciated with reference to the following detailed description when considered in connection with the following drawings. The drawings are presented for the purpose of illustration only and are not intended to be limiting, in which.

DETAILED DESCRIPTION

Figure 1:
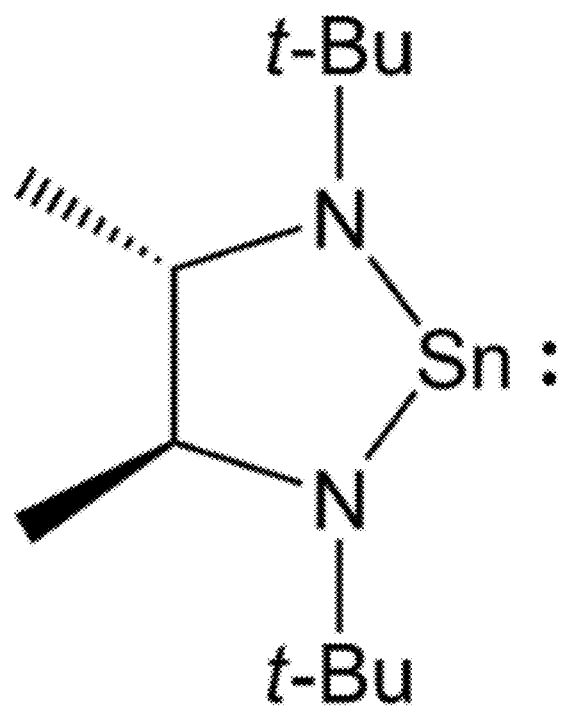
FIG. 1 shows a molecular structure of a Sn precursor in accordance with certain embodiments.

The present disclosure provides novel volatile compounds containing tin or lead bound to a cyclic amide ligand. The present disclosure also includes the use of these compounds for preparing materials by vapor deposition from reactants including cyclic amides. In an atomic layer deposition (ALD) process, doses of the amide compound vapor are supplied to a surface alternately with a vapor of a second reactant. An exemplary ALD apparatus suitable for use in ALD depositions include that shown U.S. Pat. No. 7,557,229, which is hereby incorporated by reference herein. In a chemical vapor deposition (CVD) process, the amide compound vapor is mixed with the vapor of the second reactant. Commercially available ALD and CVD systems can also be used.

Typical second reactants include hydrogen gas, ammonia gas or water vapor. When a reducing gas such as hydrogen gas is chosen as the second reactant, elemental tin or lead may be deposited. When a nitrogen-containing gas such as ammonia gas or hydrazine vapor is chosen as the second reactant, a nitride is deposited. When an oxygen-containing second reactant, such as hydrogen peroxide, water vapor, oxygen, dinitrogen tetroxide, or ozone is chosen as the second reactant, a metal oxide is deposited. When a sulfur-containing second reagent, such as hydrogen sulfide or bis(tert-butyl)sulfide, is used, a sulfide is deposited.

One or more embodiments of the present disclosure include volatile cyclic amides. One class of these compounds has a formula 1,

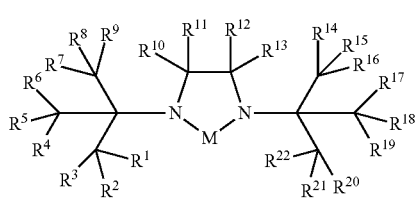

in which the metal M is tin or lead, and in which the R"s may be chosen independently from hydrogen, alkyl, cycloalkyl, alkenyl, alkynyl, trialkylsilyl, fluoroalkyl groups or alkyl groups substituted by other non-metal atoms or groups. In certain embodiments, the R"s are each independently hydrogen or alkyl groups containing 1 to 4 carbon atoms.

In certain embodiments, in the general formula 1, $R^{10}$ and $R^{12}$ are methyl groups, the other R"s are hydrogen, and the metal M is tin or lead. Isomers of the tin compound may be described by the formula 2,

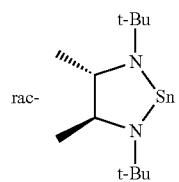

In certain embodiments, the structure of the metal amide is selected to promote vaporization without significant decomposition. Without wishing to be bound by theory, smaller R groups can provide compounds of smaller molecular weight that favor volatility. However, smaller R groups can also lead to interactions, such as dimerization or polymerization, which can increase the molecular weight. Such increase in molecular weight can reduce volatility and can increase the likelihood that the compounds will decompose before significant vaporization occurs. Accordingly, selecting suitable R groups that provide large enough steric hindrance to prevent interactions while also affording sufficient volatility are provided in certain embodiments of the present disclosure.

Vaporization and decompositions temperatures can be readily determined using conventional techniques, such as thermogravimetric analysis (TGA) and differential scanning calorimetry (DSC). In one or more embodiments, the metal amide compounds of the present disclosure can be vaporized during TGA with less than 5 weight % nonvolatile residue (in which the residue is an indication of decomposition). In certain embodiments, the non-volatile residue is less than 2 wt %, or even less than 1 wt %.

In certain embodiments, the metal amide structure can also be selected to provide compounds having a decomposition temperature, that is at a higher temperature than the vaporization temperature. For example, the decomposition temperature is at least 20° C. higher than the vaporization temperature. In certain embodiments, the decomposition temperature is at least 50° C. higher than the vaporization temperature. In certain embodiments, the decomposition temperature is at least 100° C. higher than the vaporization temperature.

In certain embodiments, the metal amide structure can also be selected to provide compounds having high volatility, such as a compound having a vapor pressure greater than 0.1 Torr at a temperature less than 200° C. In certain embodiments, the vapor pressure can be greater than 1 Torr at a temperature less than 100° C. In certain embodiments, the vapor pressure can be greater than 1 Torr at a temperature less than 50° C.

One aspect of the metal amide structure that may be beneficial to obtaining successful vaporization is the presence of a tertiary carbon attached to each nitrogen atom. The large steric bulk of the tertiary alkyl groups may be able to hinder the molecules from dimerizing or polymerizing.

In one or more embodiments, the compounds have sufficient volatility to be useful in a vapor deposition process. Therefore, in certain embodiments, the R groups are independently selected to contain at most 4 carbons. In some other embodiments, the each R groups are independently chosen to be hydrogen atoms or methyl groups, while at the same time discouraging side reactions such as polymerization that can reduce volatility and increase the likelihood of decomposition.

The cyclic amides may be prepared using any suitable method. One method can involve first forming a dilithium diamide by reaction of a diazadiene with an alkyllithium compound:

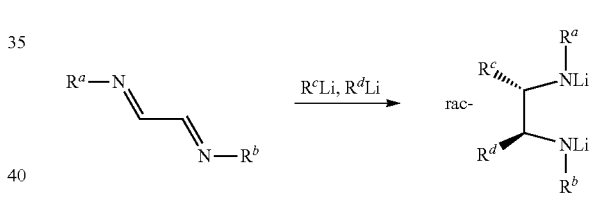

Then the dilithium diamide can be reacted with a metal dihalide to form a metal cyclic amide:

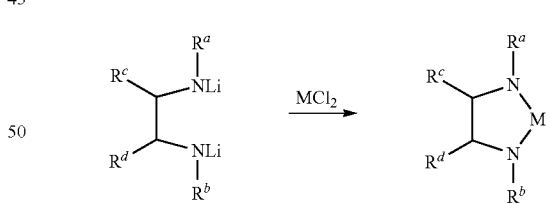

For example, synthesis of the compound of formula 2 can involve first forming a dilithium diamide by reaction of 2,2,7,7-tetramethyl-3,6-diaza-3,5-octadiene with methyllithium:

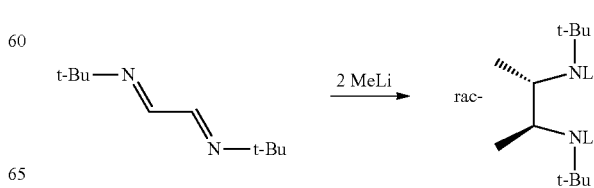

The resulting dilithium diamide can then be reacted with tin dichloride in cold diethyl ether:

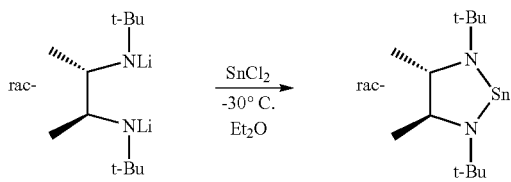

The byproduct lithium chloride can be filtered off, and the crude product can be purified by crystallization or sublimation.

According to one or more embodiments, a metal amide can be introduced onto a substrate as a vapor. Vapors of precursors may be formed by conventional methods from either liquid or solid precursors. In one or more embodiments, a liquid precursor may be vaporized by nebulization into a carrier gas preheated above the vaporization temperature, e.g., to about 50 to 200° C. The nebulization may be carried out pneumatically, ultrasonically, or by other suitable methods. Solid precursors to be nebulized may be dissolved in organic solvents, including hydrocarbons such as decane, dodecane, tetradecane, toluene, xylene, mesitylene, tetrahydronaphthalene, alloocimene, myrcene and farnesene, ethers, esters, ketones and chlorinated hydrocarbons. Solutions of liquid precursors generally have lower viscosities than pure liquids, so that in some cases it may be preferable to nebulize and evaporate solutions rather than pure liquids. The precursor liquid or precursor solutions may also be evaporated with thin-film evaporators, by direct injection of the liquids or solutions into a heated zone, or by heating in a bubbler. Commercial equipment for vaporization of liquids is made by MKS Instruments (Andover, Mass.), ATMI, Inc. (Danbury, Conn.), Novellus Systems, Inc. (San Jose, Calif.), COVA Technologies (Colorado Springs, Colo.), Brooks Instrument (Hatfield, Pa.), Horiba Stec (Kyoto, Japan) and Kemstream (Montpellier, France). Ultrasonic nebulizers are made by Sonotek Corporation (Milton, N.Y.) and Cetac Technologies (Omaha, Nebr.).

The precursors of the present disclosure may be reacted with a reducing agent, e.g., hydrogen gas, to form films of tin or lead. The precursors of the present disclosure may be reacted with an oxidizing agent, e.g. oxygen, ozone, hydrogen peroxide, dinitrogen tetroxide, or water, to form oxide films. The precursors of the present disclosure may be reacted with a sulfur-containing reagent, e.g. hydrogen sulfide or di-tert-butyl disulfide, to form sulfide films. The precursors of the present disclosure may be reacted with a nitrogen-containing reagent, e.g. ammonia or hydrazine, to form nitride films.

In certain embodiments, the process of the present disclosure may be carried out using atomic layer deposition (ALD). ALD introduces a metered amount of a first reactant into a deposition chamber having a substrate therein for layer deposition. A thin reaction product of the first reactant can be deposited on the substrate. Then, any unreacted first reactant and volatile reaction by-products can be removed by a vacuum pump and, optionally, a flow of inert carrier gas. A metered amount of a second reactant component can then be introduced into the deposition chamber. The second reactant can deposit on and react with the already deposited layer from the first reactant. Alternating doses of first and second reactants can be introduced into the deposition chamber and deposited on the substrate to form a layer of controlled composition and thickness. The time between doses may be on the order of seconds and can be selected to provide adequate time for the just-introduced component to react with the surface of the film and for any excess vapor and byproducts to be removed from the headspace above the substrate. It has been determined that the surface reactions are generally self-limiting so that a reproducible layer of predictable composition is deposited. As will be appreciated by one of ordinary skill in the art, deposition processes utilizing more than two reactant components are within the scope of the invention.

The metal compounds produced by these procedures can generally react with moisture and/or oxygen in the ambient air, and may be stored and handled under an inert, dry atmosphere such as pure nitrogen or argon gas.

EXAMPLES

Example 1

Synthesis of Tin Compound of Formula 2

To 50 ml (0.80 mol, 1.6 M in ether) of methyl lithium in 250 ml of cold (−30° C.) ether was added 6.73 g (40 mmol) of 2,2,7,7-tetramethyl-3,6-diaza-3,5-octadiene in several portions (some heat evolution) and the mixture was stirred at room temperature for ca. 1.5 hours. This solution was recooled to −30° C. and $SnCl_2$ (7.58 g, 40 mmol) was added in portions with vigorous stirring. The mixture was allowed to warm to room temperature and filtered. The solvent was removed in vacuo. Analytically pure material may be obtained by crystallization from concentrated pentane solutions at −30° C. or by sublimation (60° C., ~0.03 mmHg) onto a −78° C. cold finger. Yield 6.85 g (54%) of a yellow solid. $^1H$ NMR ($C_6D_6$, 400 MHz): δ 3.32 (q, $J_{C-H}$ 6.0 Hz, 2H, CHMe), 1.25 (s, 18, $CMe_3$), 1.19 (d, $J_{C-H}$ 6.0 Hz, 6H, backbone Me). $^{13}C$ NMR ($C_6D_6$, 100 MHz): δ64.476, 56.075, 34.208, 28.714. Anal. Calc for $C_{12}H_{26}N_2Sn$: C, 45.46; H, 8.27; N, 8.84. Found: C, 45.35, 45.32; H, 8.17, 8.14; N, 8.66, 8.63.

A crystal of formula 2 was structurally characterized by X-ray crystallography. The structure, shown in FIG. 1, is a monomer in the solid state. The average Sn—N distance is 2.02 Å and the N—Sn—N angle is 82.7°.

Figure 2:
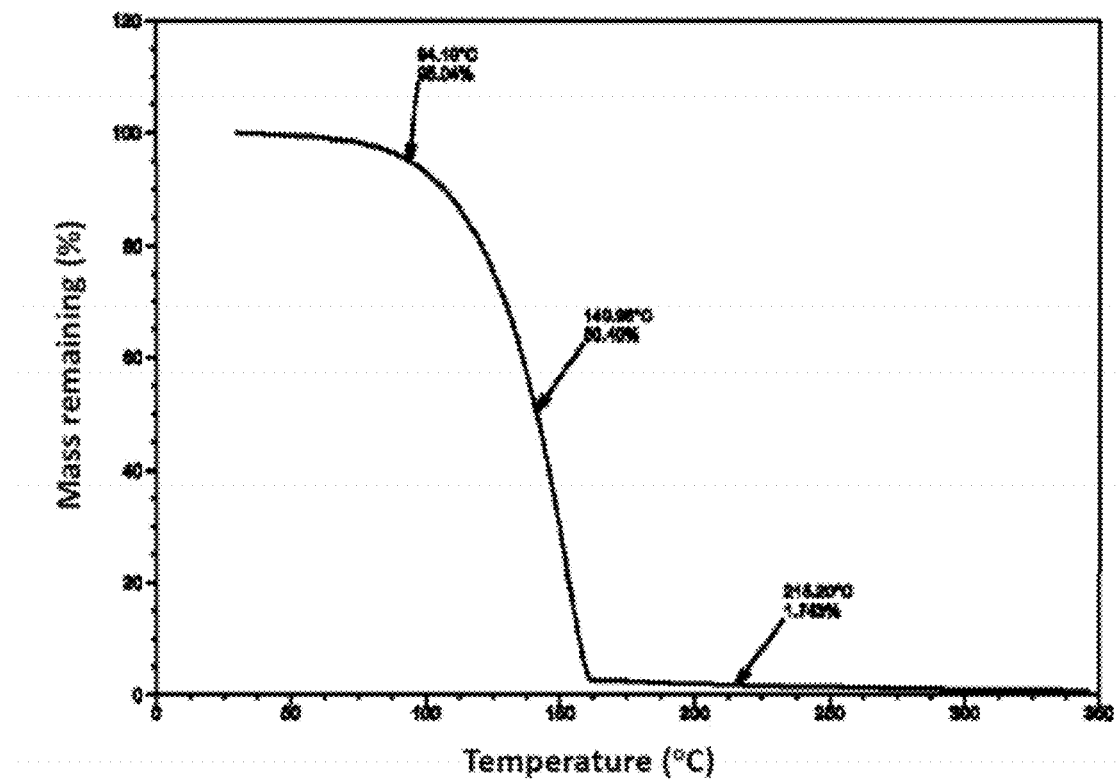
FIG. 2 shows a thermogravimetric analysis of a Sn precursor in accordance with certain embodiments.

Thermogravimetric analysis of tin compound of formula 2 was carried out in one atmosphere of flowing nitrogen, giving the results shown in FIG. 2. These data show a clean evaporation in one step with low residue (<1.7%). These properties are desirable in a precursor for use in vapor deposition.

Without wishing to be bound by theory, divalent tin precursors have fewer ligands than conventional tetravalent tin sources, which can reduce the molecular weight of the complex and can increase the vapor pressure of the precursor.

Reactivity of the compound of formula 2 was tested in solution as a preliminary predictor of its reactivity for vapor deposition at low temperature. Reaction of the precursor with hydrogen peroxide in solution at room temperature produced a precipitate of white $SnO_2$ with no sign of black SnO, indicating complete oxidation of the Sn(II) precursor to Sn(IV). Solution reactivity is a simple yet powerful tool for the rapid evaluation and optimization of new precursors and processes for vapor deposition at low temperatures.

Without wishing to be bound by theory, the choice of a divalent tin precursor may engender high reactivity because its relatively open molecular structure can provide easy access of co-reactants to the tin atoms. Based on this test of solution reactivity, ALD of SnO$_2$ using tin compound of formula 2 and hydrogen peroxide was carried out as described below in Example 2.

Example 2

Deposition of Tin Oxide Films by ALD with H$_2$O$_2$ as the Oxygen Source

The stannylene diamide compound of formula 2 was placed in a stainless steel container with a vapor volume of 125 cubic centimeters and heated to 40° C., at which temperature it has a vapor pressure of about 1.2 Torr. Doses of 7.7 micromoles of the tin precursor were introduced by pressurizing the container to 10 Torr with nitrogen carrier gas, and then releasing the gas mixture into the reactor for 1 second. Hydrogen peroxide, 50 wt. % in H$_2$O, (Sigma Aldrich) was used as received. H$_2$O$_2$ was vaporized into a trap volume (35 mL) made of stainless steel and subsequently delivered to the reaction chamber. The "exposure" refers to the product of the partial pressure of a precursor vapor in the deposition zone and the time that this vapor is in contact with a given point on the surface of the substrate. The exposure of the substrate to the tin precursor was 1.2 Torr-seconds/dose and its exposure to hydrogen peroxide was 1.25 Torr-seconds/dose. The amount of precursor and H$_2$O$_2$ in each ALD cycle was varied by changing the number of injections during each cycle. All precursor and oxidant injections were computer-controlled by air-operated valves. One growth cycle consists of four steps: exposure to a certain number (between 1 and 6) of doses of the Sn precursor, purge of the precursor, exposure to a certain number (between 1 and 6) of doses of H$_2$O$_2$, and purge of the oxidant. The injection and purge times for each step were optimized to be 1, 25, 6, 45 s, respectively.

The resistivity of films deposited on 300 nm-thick thermal oxide/Si substrates was evaluated using a four-point probe, and also corroborated by using the Van der Pauw method. The measurement of film thickness and refractive index was performed on a spectroscopic ellipsometer (Woollam, WVASE32). On HF-dipped, H-terminated Si substrate, retardation of nucleation equal to about 25 cycles was observed. For enhancing the nucleation process, Si substrates were oxidized by UV-ozone treatment under a mercury discharge lamp in air. Substrates of glassy carbon were cleaned with 10% aq. HF (5 s), deionized water (30 s), and isopropanol (10 s) prior to drying and UV cleaning for 5 minutes. Substrates of glass were cleaned with isopropanol (10 s), dried and subjected to UV-ozone cleaning for 2 minutes. Surface morphology of the deposited SnO$_2$ film was observed by using field-emission scanning electron microscopy (FESEM, Zeiss, Ultra 55) and atomic force microscopy (AFM, Asylum, MFP-3D SA). The crystallinity and crystallographic orientation of a SnO$_2$ film on a glass substrate was determined by X-ray diffraction (Scintag, XDS 2000, Cu K$_\alpha$). High-resolution transmission electron microscopy (HRTEM, Jeol, JEM-2100) was also employed for evaluation on film microstructure. The majority carrier type, carrier concentration, and mobility in the temperature range of 80-350 K were investigated by Hall measurement (Ecopia, HMS-3000). The film composition and impurity incorporation were checked by X-ray photoelectron spectroscopy (XPS, Surface Science, SSX-100) and Rutherford backscattering spectroscopy (RBS). The film density was evaluated by combining RBS and X-ray reflectivity (XRR). Optical transmission of the film was measured by a UV-Vis spectrophotometer (Hitachi, U-4001).

Figure 3A:
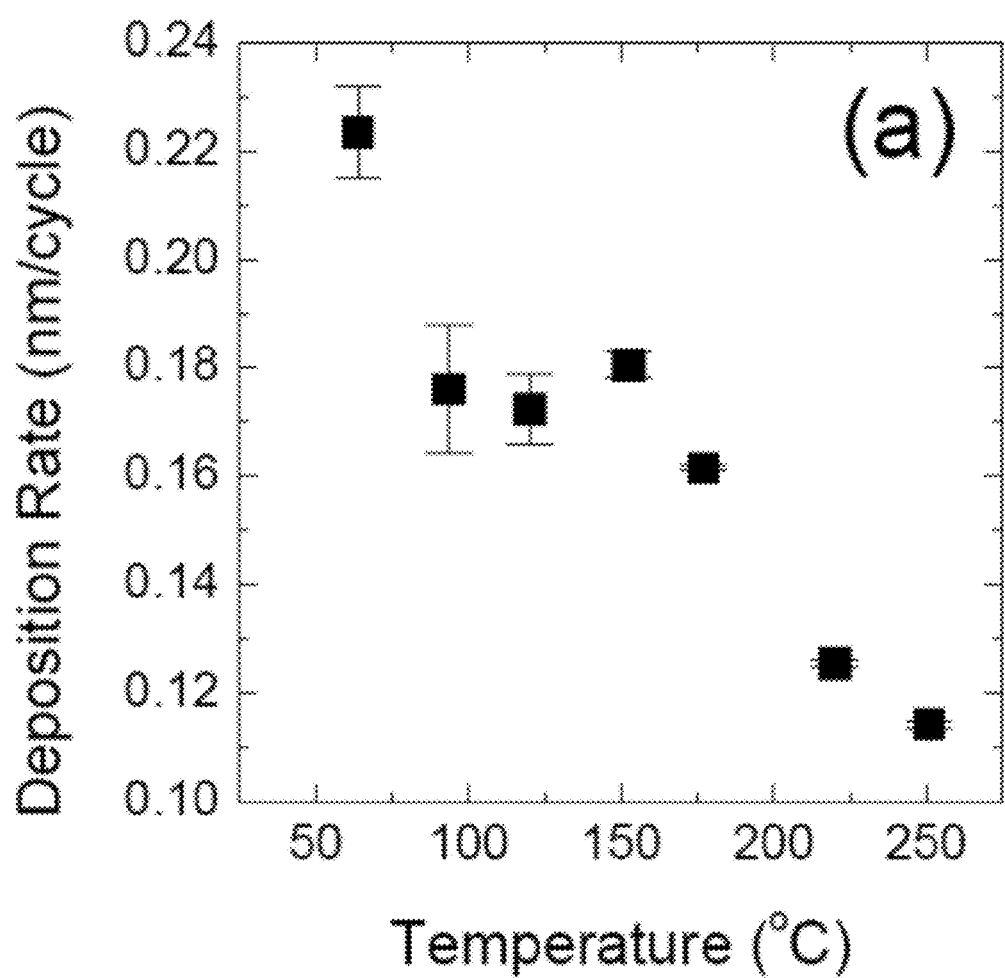
FIG. 3(a) shows the film growth rate as a function of the deposition temperature in accordance with certain embodiments.
Figure 3B:
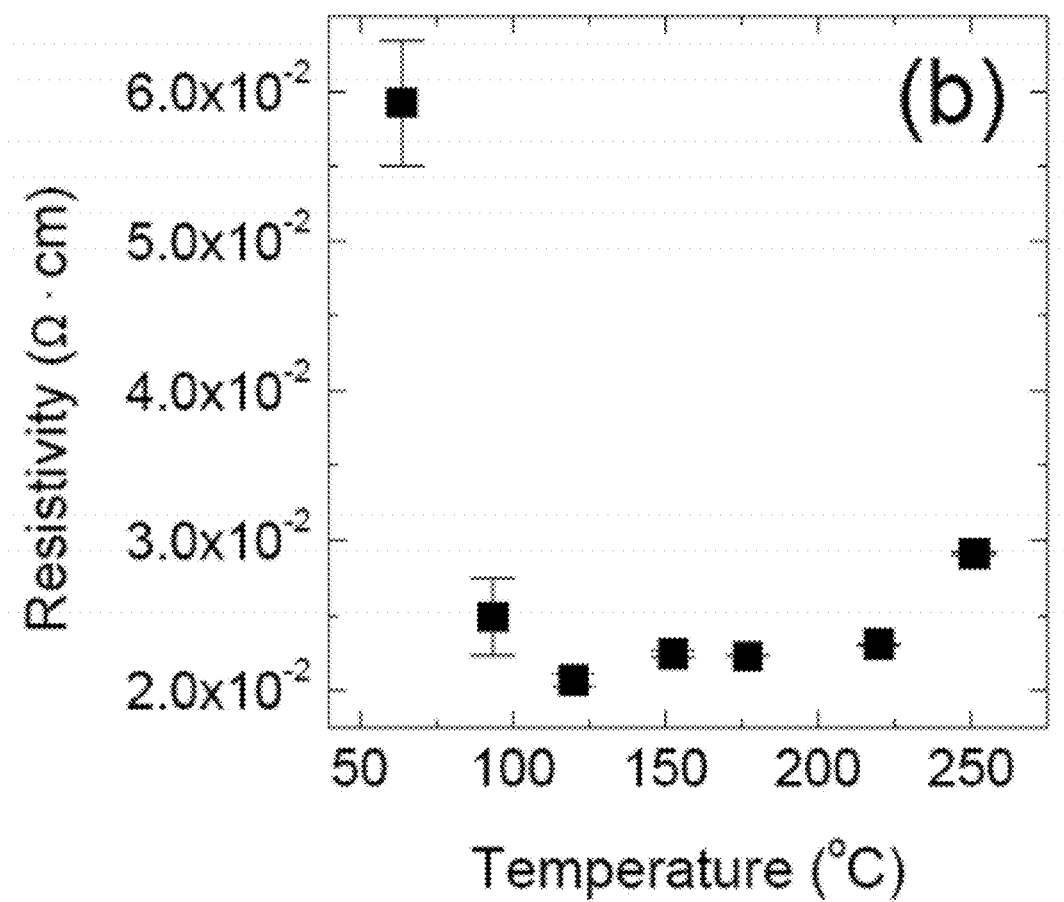
FIG. 3(b) shows the film resistivity as a function of the deposition temperature in accordance with certain embodiments.

Using the Sn precursor of formula 2 and H$_2$O$_2$ in the ALD process described above, films of conductive SnO$_2$ were obtained on substrates held at temperatures from about 50-200° C. Successful growth was carried out on plastic substrates (epoxy and polyimide), metals (aluminum and stainless steel), oxides (silica, alumina and glass), and oxidized silicon and glassy carbon. From 50° C. to 150° C. the growth rate was constant at around 0.18 nm/cycle. At substrate temperatures above 150° C. the deposition rate decreased with increasing temperature. FIG. 3(a) shows the ALD growth per cycle as a function of the deposition temperature. At temperatures above 150° C., a decreasing number of surface hydroxyl groups, which subsequently act as adsorption sites for Sn precursors, appears to limit the amount of growth. The refractive index of all films is ~1.95, close to the bulk SnO$_2$ value of 2.04. FIG. 3(b) shows the film resistivity as a function of the deposition temperature. The film thicknesses measured by ellipsometry were used to calculate the film resistivity from sheet resistance measured by using four-point probe method. The film resistivity remains 2-3× 10$^{-2}$ ohm cm except for the film grown at 63° C. Although the growth rate decreased with increasing the deposition temperature above 150° C., there was no prominent increase in the film resistivity. Based on these growth rate and film resistivity data, the deposition temperature of the following experiments was fixed at 120° C.

Figure 4A:
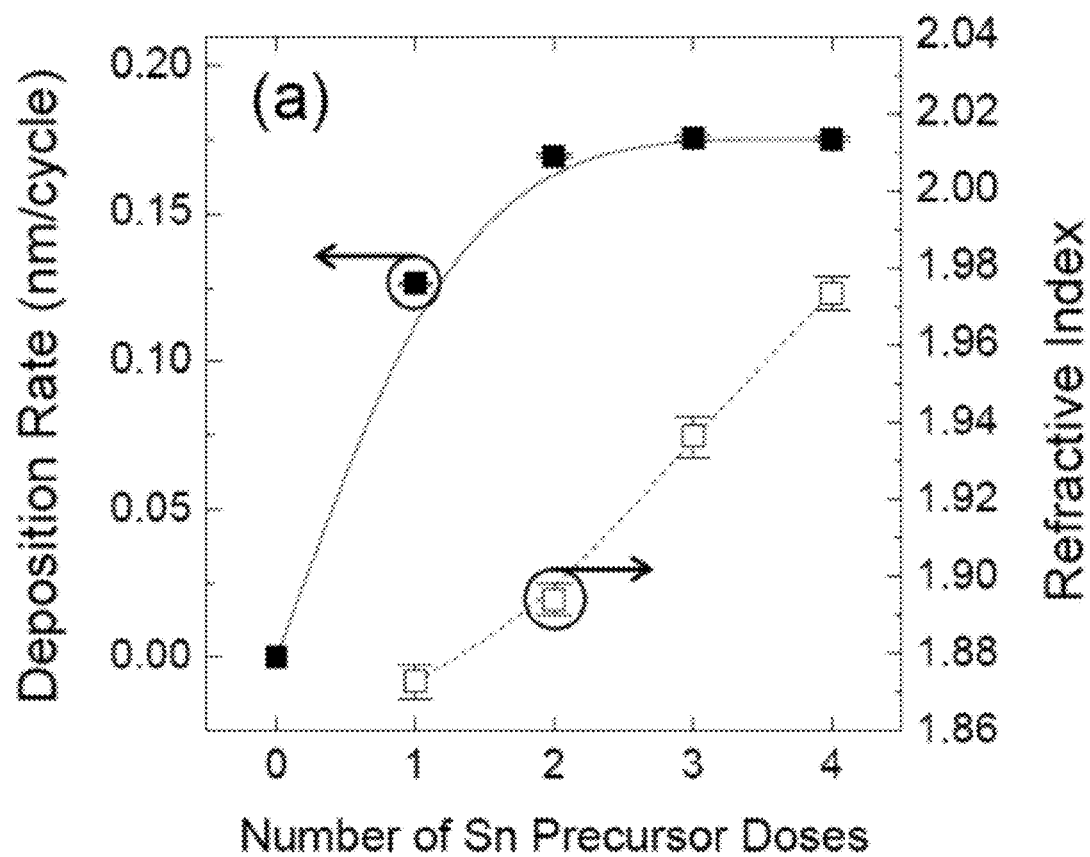
FIG. 4(a) shows the changes in the growth rate and refractive index with different numbers of injection for Sn precursor where the number of injections for $H_2O_2$ was maintained at three times in accordance with certain embodiments.
Figure 4B:
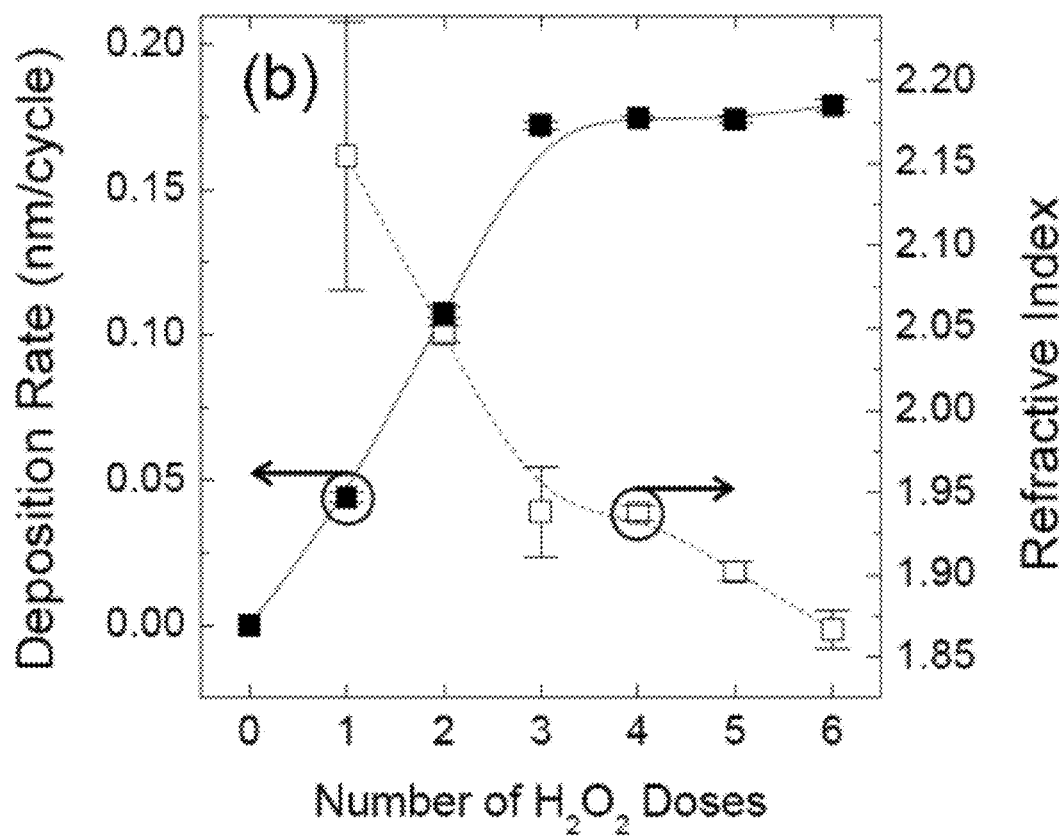
FIG. 4(b) shows the changes in the growth rate and refractive index with different numbers of injection for $H_2O_2$ where the number of injections for $H_2O_2$ was maintained at three times in accordance with certain embodiments.
Figure 4C:
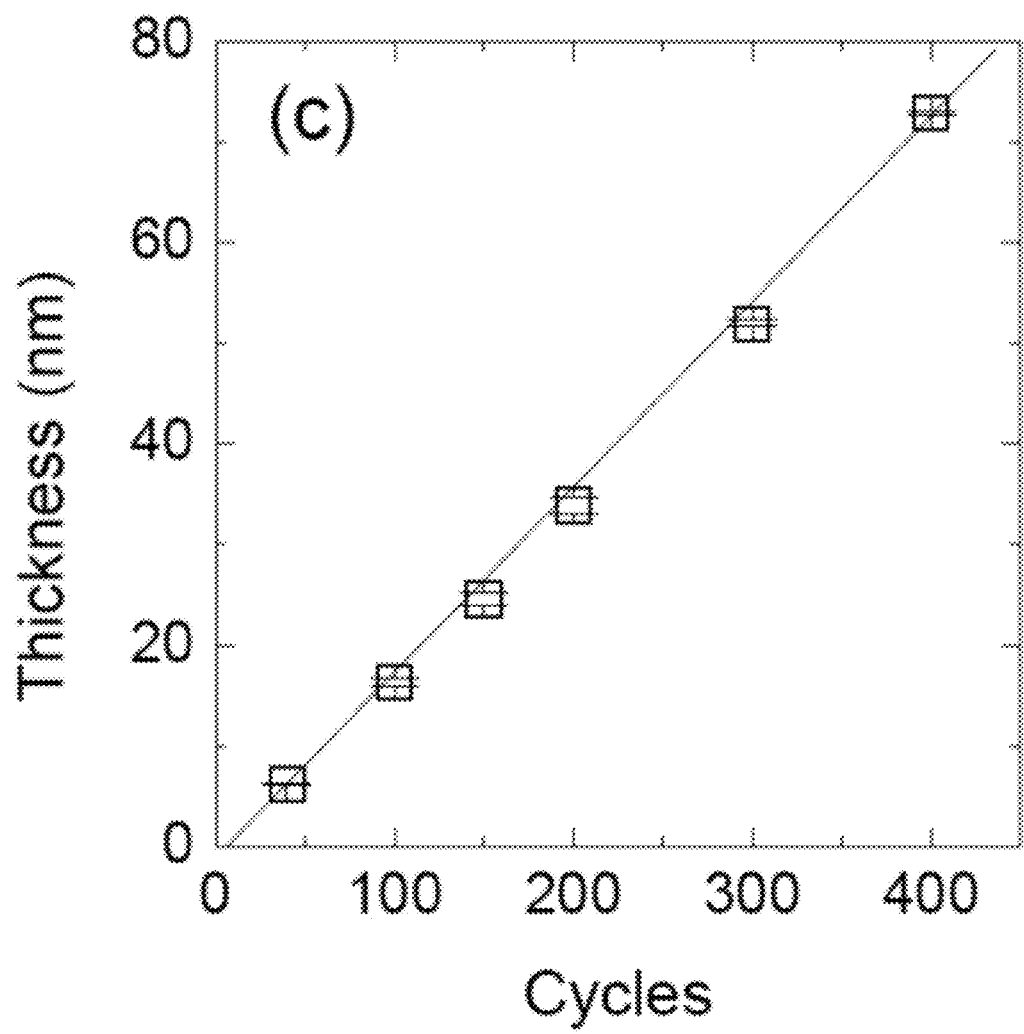
FIG. 4(c) shows the variation in the thickness of the $SnO_2$ films for injection of the Sn precursor and $H_2O_2$, each three times, as a function of the growth cycle on a Si substrate with native oxide in accordance with certain embodiments.

FIG. 4 shows the changes in the growth rate and the refractive index with different numbers of doses of (a) Sn precursor and (b) H$_2$O$_2$, respectively. Here, H$_2$O$_2$ and Sn precursors were each injected three times for each experiment. It was shown in the figure that three injections of both Sn precursor and oxidant pulse is enough to obtain the saturated ALD growth rate. The experimental results discussed below employed this condition if it is not mentioned specifically. These results show that the surface reactions are self-limiting. The linear plot of the film thicknesses as a function of the number of the growth cycles is shown in FIG. 4(c). Here, the thickness data are reduced by 2 nm, which corresponds to the thickness of native oxide on a Si substrate. This figure clearly indicates that the film thickness is directly proportional to the number of ALD cycles, which is the characteristic behavior of layer-by-layer growth in ALD. From the slope, the obtained growth rate was 0.175 nm/cycle, which was the highest ALD SnO$_2$ growth rate reported so far at a growth temperature of 120° C. From the small value of the intercept near the origin, it was observed that nucleation takes place promptly on the substrates, with little, if any, delay. Thus any induction period is not more than a few cycles long. The film density was estimated to be ~5.61-5.80 g/cm$^3$ for the film grown by using 3 doses of the Sn precursor and of H$_2$O$_2$. Given the theoretical density of 6.95-6.99 g/cm$^3$ for bulk crystalline SnO$_2$, the film density obtained for three doses of H$_2$O$_2$ corresponds to 80-83% of the bulk value.

Figure 5:
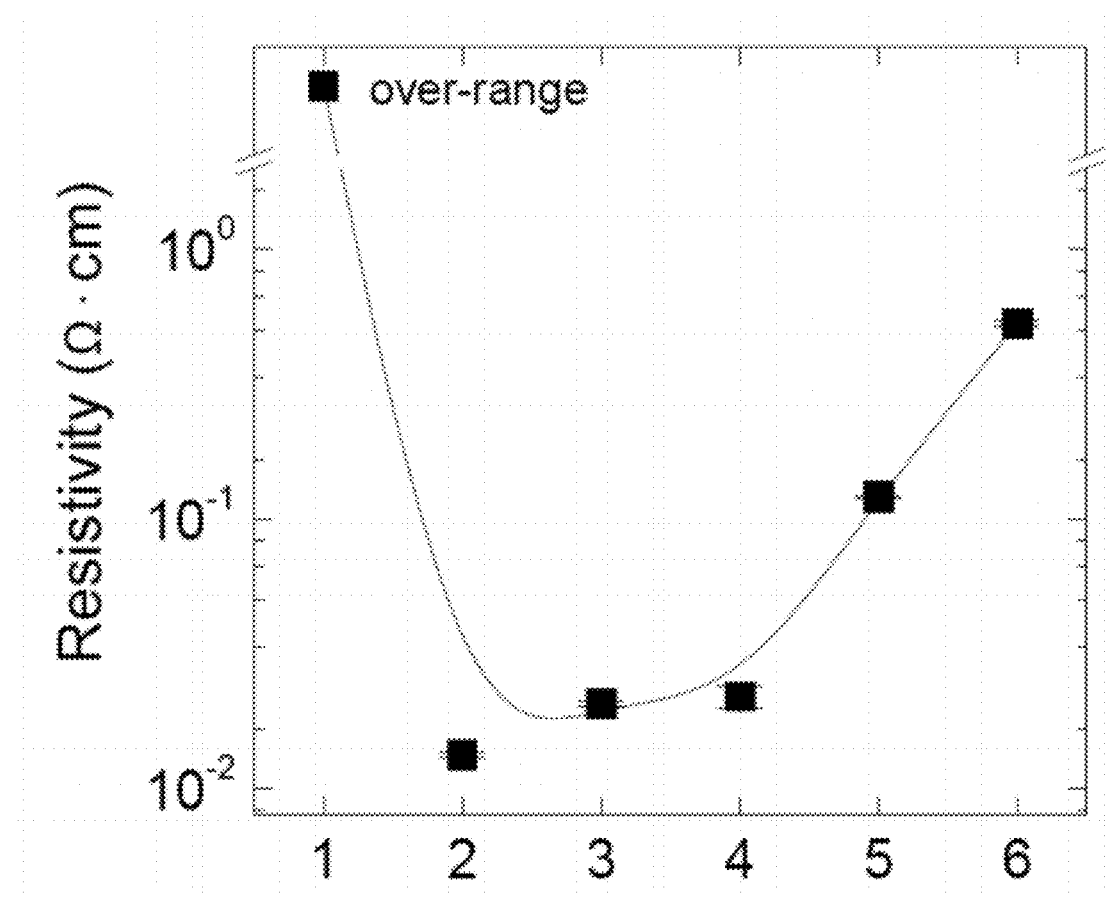
FIG. 5 shows the change in the film resistivity as a function of the number of $H_2O_2$ doses, where Sn precursor was injected three times in accordance with certain embodiments.

FIG. 5 plots the film resistivity as a function of the number of H$_2$O$_2$ doses in each cycle. When one dose of H$_2$O$_2$ was used, the sheet resistances of as-deposited films were over 10$^5$ ohms per square. This high resistance could be due to the existence of insulating SnO or Sn$_3$O$_4$ phases based on the high refractive index of these films (~2.15). With the introduction of two H$_2$O$_2$ doses, the film shows the lowest resistivity of 1.33×10$^{-2}$ ohm·cm. However, the saturation of growth rate was not observed for this condition although it is as high as 0.11 nm/cycle. The electrical conductivity of SnO$_x$ can result from the existence of oxygen vacancies, which act as majority electron donors. As discussed later, it turned out that the film with two H$_2$O$_2$ doses was oxygen deficient where the O/Sn ratio was less than 2. When the number of hydrogen peroxide doses are in the range of two to four times of $H_2O_2$ dose, the resistivity remains in the range $1$-$3\times10^{-2}$ ohm cm. The growth rate was saturated when the number of $H_2O_2$ doses was higher than three, but the film resistivity gradually increased with increasing the number of $H_2O_2$ doses: $2.2\times 10^{-2}$, $1.2\times10^{-1}$, and $5.3\times10^{-1}$ ohm cm for four, five, and six doses of $H_2O_2$, respectively. Regarding the saturation in the growth rate over three times dose of $H_2O_2$, it appears that more injection of the oxidant makes film closer to stoichiometric $SnO_2$ or even stuffing additional oxygen species into the grain boundaries, which would make film electrically more insulating.

The carrier concentration and the mobility of the $SnO_2$ films were estimated by Hall measurement. The carrier concentration was $(-)8.1$-$9.3\times10^{19}$ cm$^{-3}$. The negative sign confirms that electrons are majority carriers of the deposited $SnO_2$ films. The mobility of the $SnO_2$ film was 6.4-7.4 cm$^2$/V·s at room temperature. The obtained electrical properties, i.e., carrier concentration, mobility, and resistivity, are comparable to those from the films grown at much higher temperatures of 400-500° C. using spray pyrolysis or magnetron sputtering.

Figure 6A:
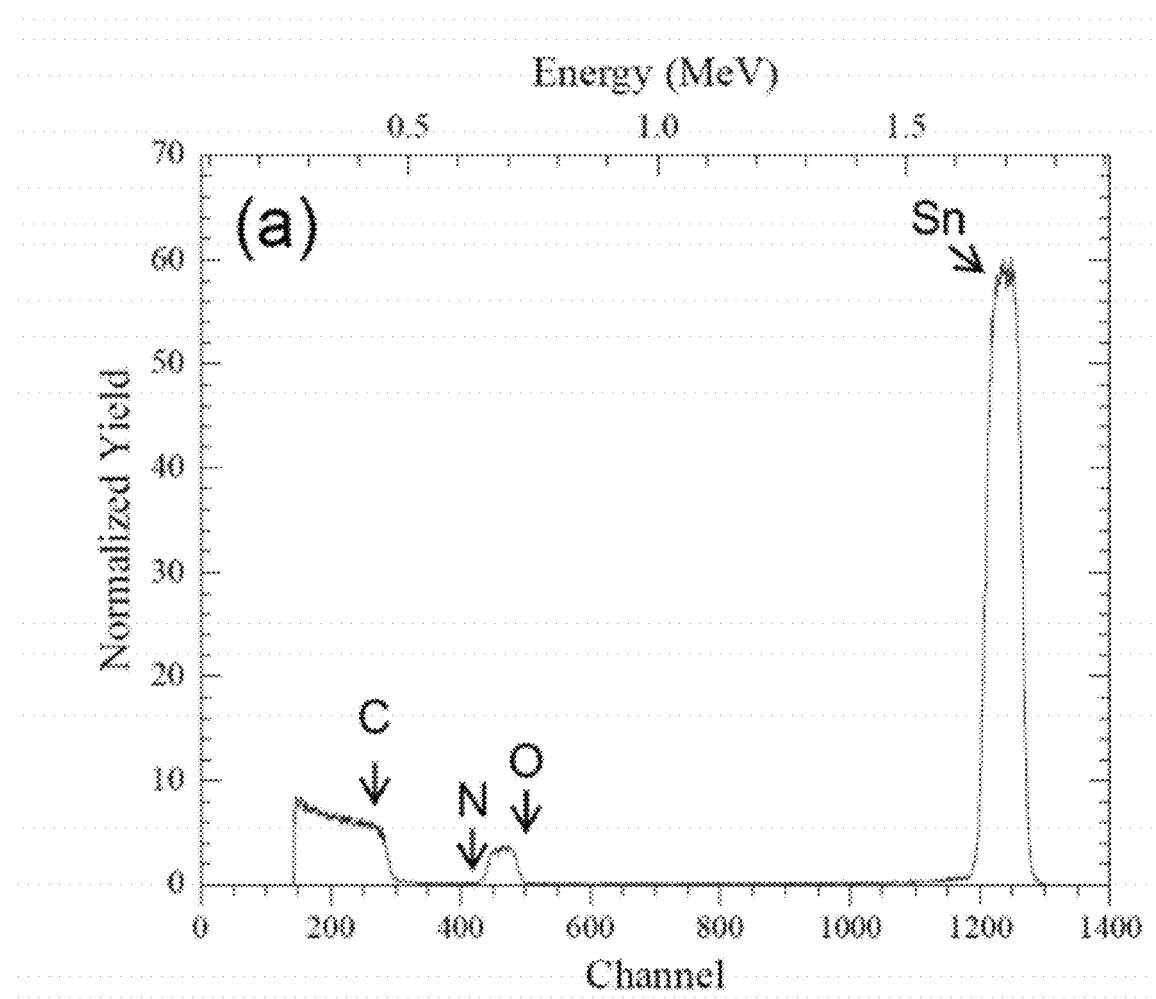
FIG. 6(a) shows a representative Rutherford backscattering spectrum of $SnO_2$ for injection of Sn precursor and $H_2O_2$, both injected three times in accordance with certain embodiments.
Figure 6B:
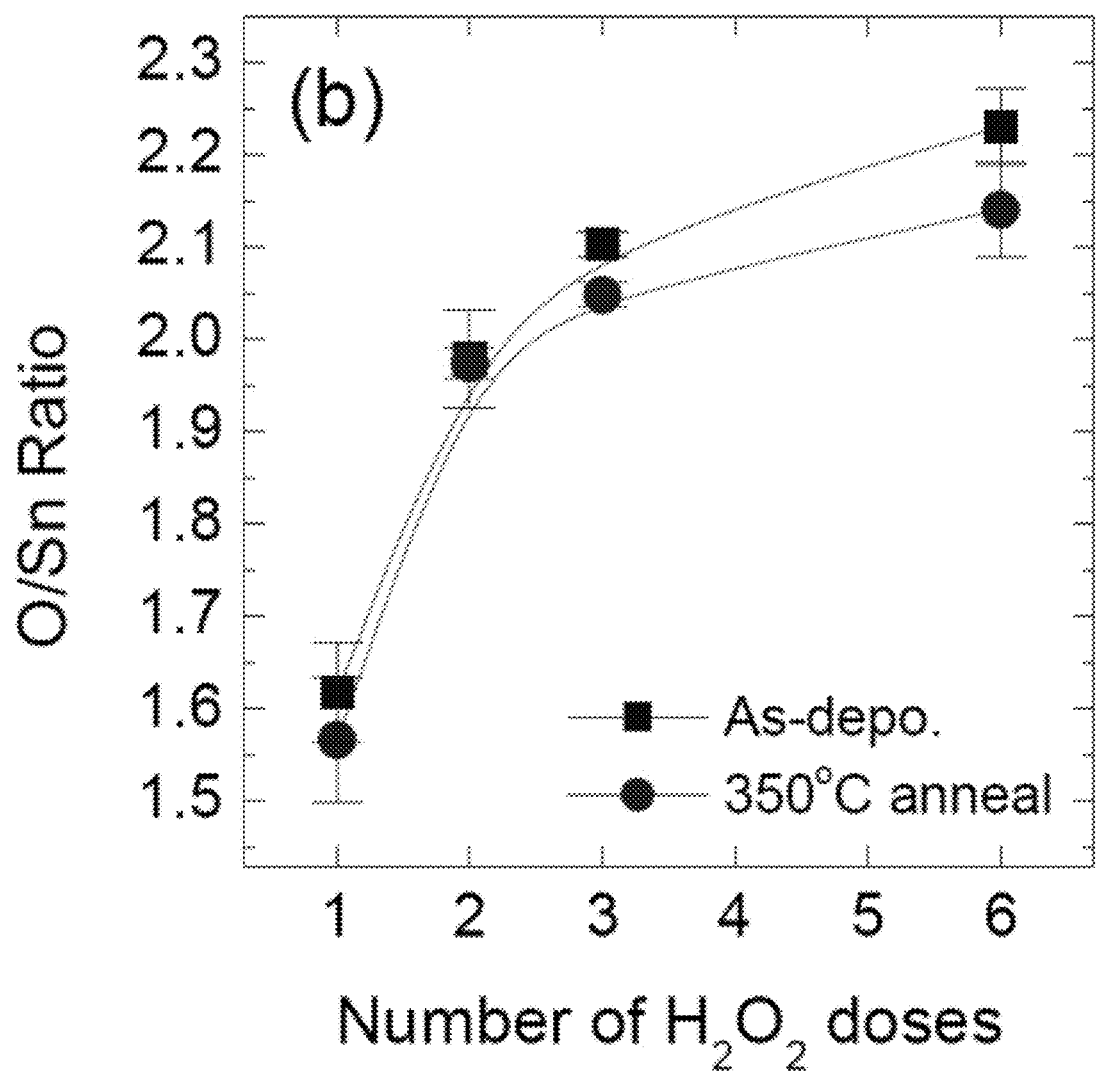
FIG. 6(b) shows the measured O/Sn ratio as a function of the number of $H_2O_2$ injections, where the closed squares and circles represent as-deposited and 350° C.-annealed films, respectively, in accordance with certain embodiments.

To understand the correlation between electrical properties of $SnO_x$ films and the number of $H_2O_2$ doses, RBS analyses were conducted. FIG. 6(a) shows a representative RBS spectrum of as-deposited $SnO_2$ film using three doses of both the Sn precursor and $H_2O_2$ on an amorphous carbon substrate. All carbon substrates experienced ultraviolet-ozone treatment for 5 min before being loaded into the chamber. Without the treatment, little film was deposited on a carbon substrate due to the paucity of surface functional groups. The O/Sn atomic ratio (calculated by from the RBS data) with different numbers of $H_2O_2$ doses is summarized in FIG. 6(b). Closed squares and circles represent as-deposited and 350° C.-$N_2$-annealed states, respectively. The impurity level of carbon and nitrogen is negligible from this measurement. When $H_2O_2$ was pulsed one time, the O/Sn ratio was $1.62\pm0.07$. It sharply increased with increasing the number of doses from one to two times ($1.98\pm0.02$). When the condition of three doses of $H_2O_2$ was used, the O/Sn ratio was $2.10\pm0.01$. When the over-saturated condition of six doses of $H_2O_2$ was used, the ratio slightly increased to $2.23\pm0.05$, although still not clearly reaching saturation. As shown in FIG. 4(b), however, the over-dose of $H_2O_2$ does not increase the growth rate, but it leads to oxygen-rich stoichiometry of $SnO_{2+x}$ state as shown by RBS. A O/Sn ratio above 2 does not indicate that the deposited film consists of a $SnO_{2+x}$ phase, because it still shows moderately low resistivity (less than 1 ohm·cm) for the cases from three to six $H_2O_2$ doses. It appears that the excessive oxygen supply partially fills oxygen vacancies and some remaining oxygen species may be interstitially doped into grains or stuffed at grain boundaries. The existence of a high portion of grain boundaries was verified by high-resolution TEM observations, as discussed later. To check the existence of thermally unstable oxygen species at grain boundaries and/or inside grains, annealing at 350° C. for 30 min was performed in a $N_2$ atmosphere. Closed circles represent the calculated O/Sn composition ratio for annealed films. The O/Sn ratio slightly decreased after the annealing, as shown in FIG. 6(b). Notably, the decrease in the ratio from $2.23\pm0.05$ to $2.14\pm0.04$ was relatively large for the condition of six $H_2O_2$ doses, whereas the other conditions show negligible decrease. This result indicates that overdose of $H_2O_2$ stuffs oxygen species into the film so that it makes film more oxygen-rich and that an over-dosed $SnO_x$ film contains more thermally unstable oxygen species than other oxygen deficient films. The relatively Sn-rich (oxygen deficient) conditions lead to the higher refractive index of the grown films. The changes in the refractive index with $H_2O_2$ dose correspond to the fact that the refractive indices of SnO and $SnO_2$ are 2.4 and 2.0, respectively.

Figure 7A:
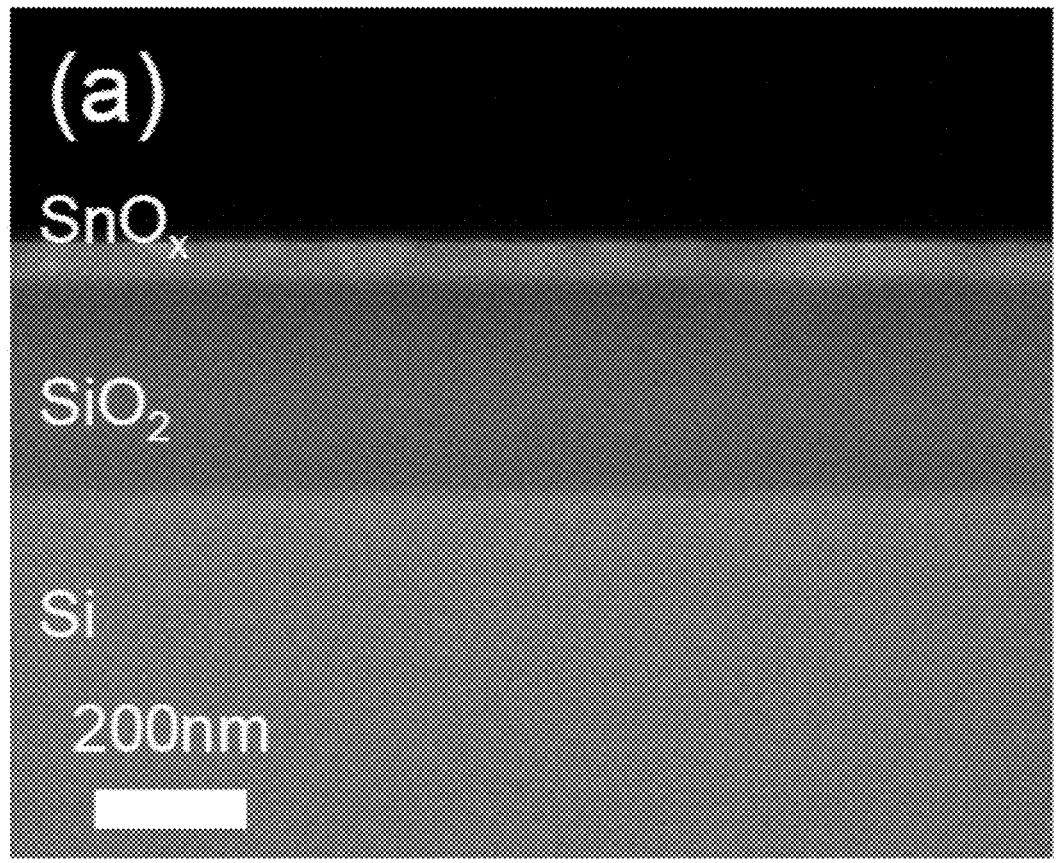
FIG. 7(a) shows a cross-section scanning electron microscopy image of $SnO_2$ film for 400 cycles deposited on a thermal oxide substrate in accordance with certain embodiments.
Figure 7B:
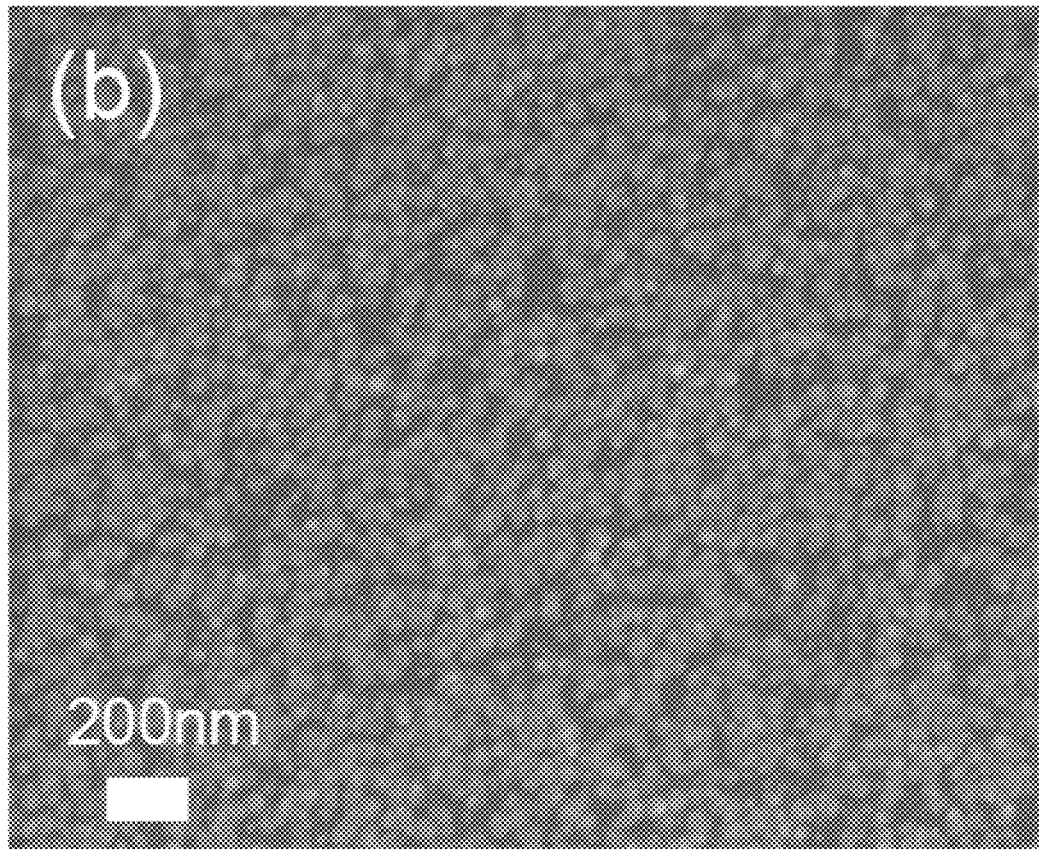
FIG. 7(b) shows its plan-view image of the $SnO_2$ film of FIG. 7(a) in accordance with certain embodiments.
Figure 7C:
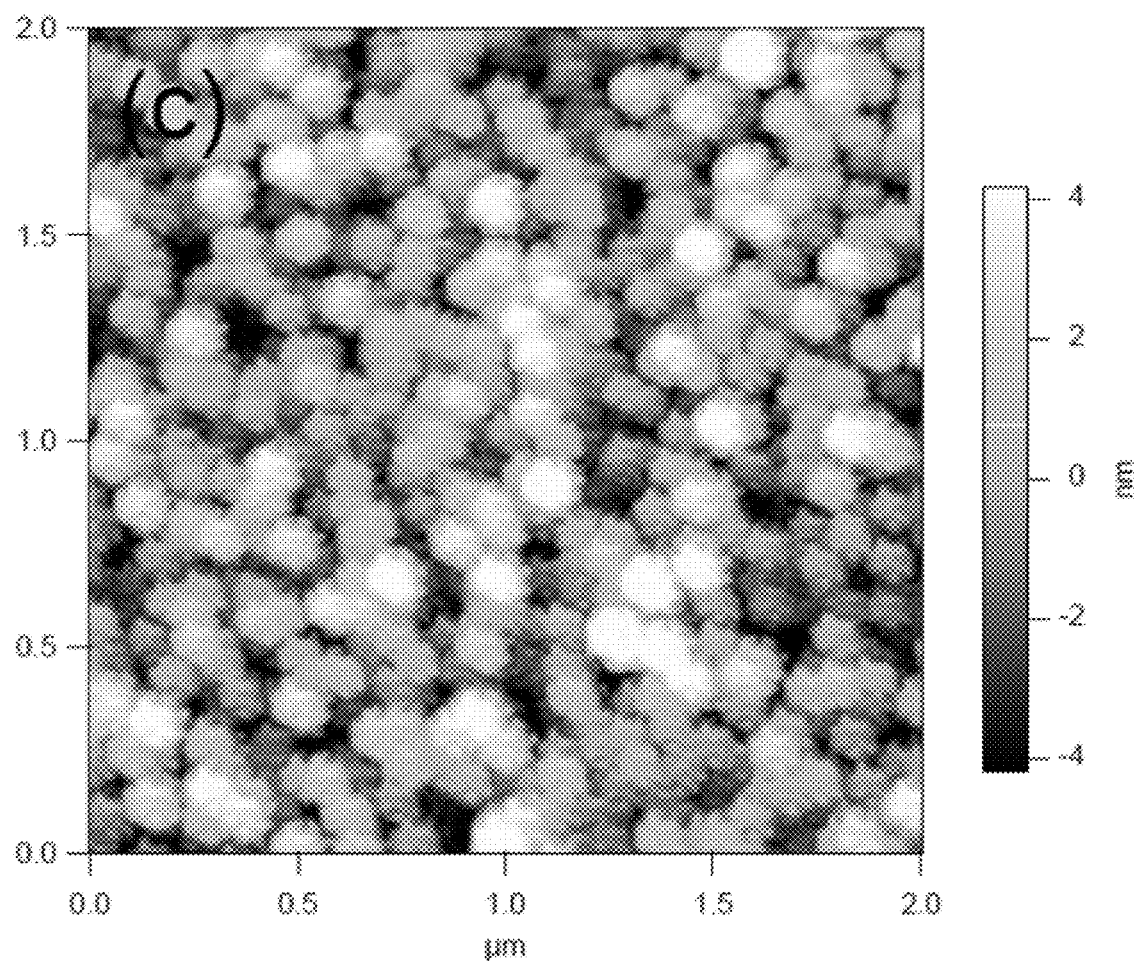
FIG. 7(c) shows an atomic force microscopy image of the $SnO_2$ film of FIG. 7(a) operating under tapping mode, where the root-mean-square roughness is estimated to be ~2 nm in accordance with certain embodiments.

FIG. 7(a) shows a cross-sectional SEM image of the $SnO_2$ film grown with the saturated condition. A 300 nm-thick thermal oxide was used as a substrate and 400 ALD cycles were used. It is seen from that figure that $SnO_2$ grows smoothly on thermal oxide. The observed thickness is 69-72 nm, which is consistent with the result (~72 nm) obtained from ellipsometry. FIG. 7(b) shows that the surface morphology of the same film consisted of small and fine grains. FIG. 7(c) shows the surface morphology of the $SnO_2$ film measured by AFM. The small and round-shaped grain structure was also demonstrated by this figure. The root-mean-square (rms) roughness was ~2 nm, which is less than 2% of the film thickness. As the number of $H_2O_2$ doses increased above three, the film became even smoother. The surface morphology appears to come from the formation of crystallites in the as-deposited state. The existence of the crystallized grains was confirmed by X-ray diffraction and transmission electron microscopy.

Figure 8A:
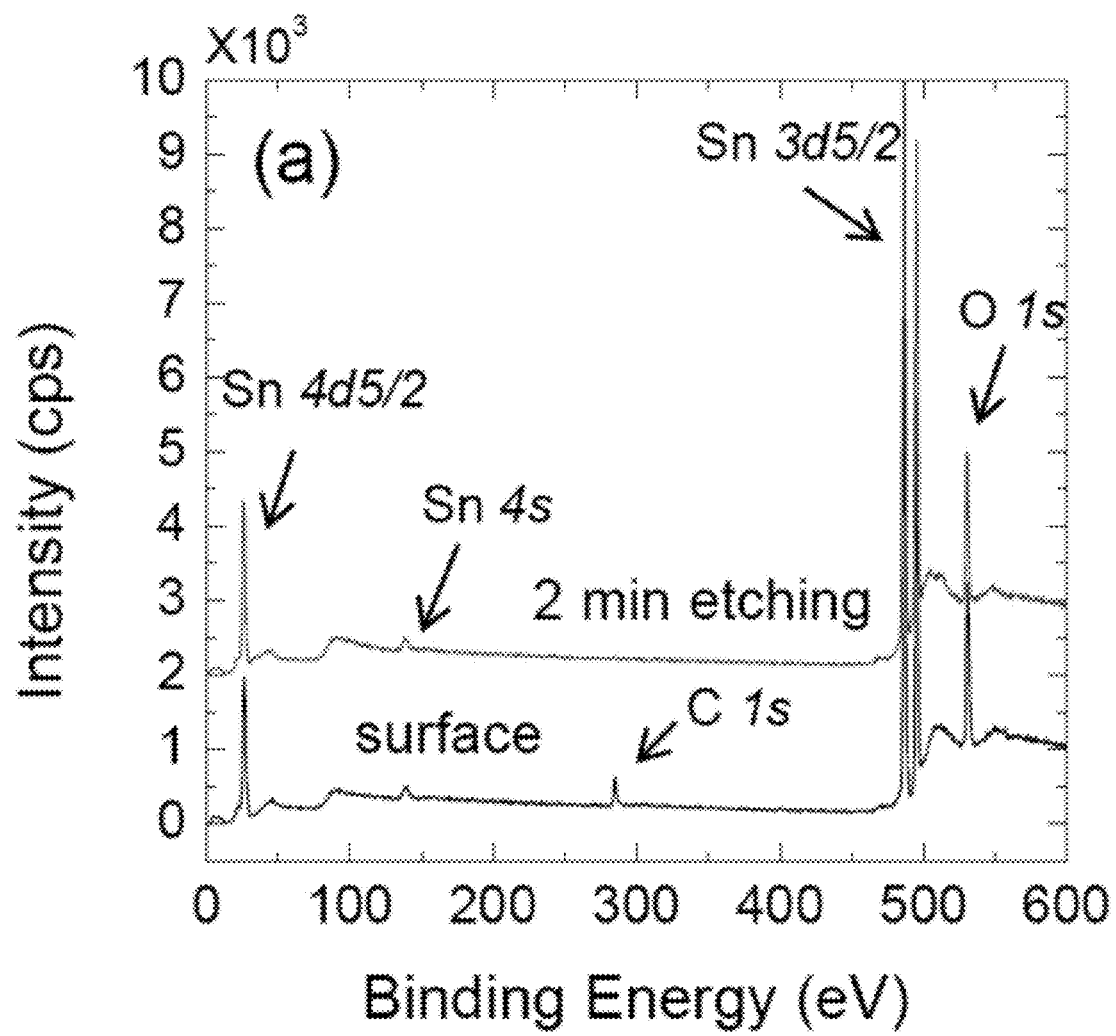
FIG. 8(a) shows survey X-ray photoelectron spectra before and after Ar etching for 2 min in accordance with certain embodiments.
Figure 8B:
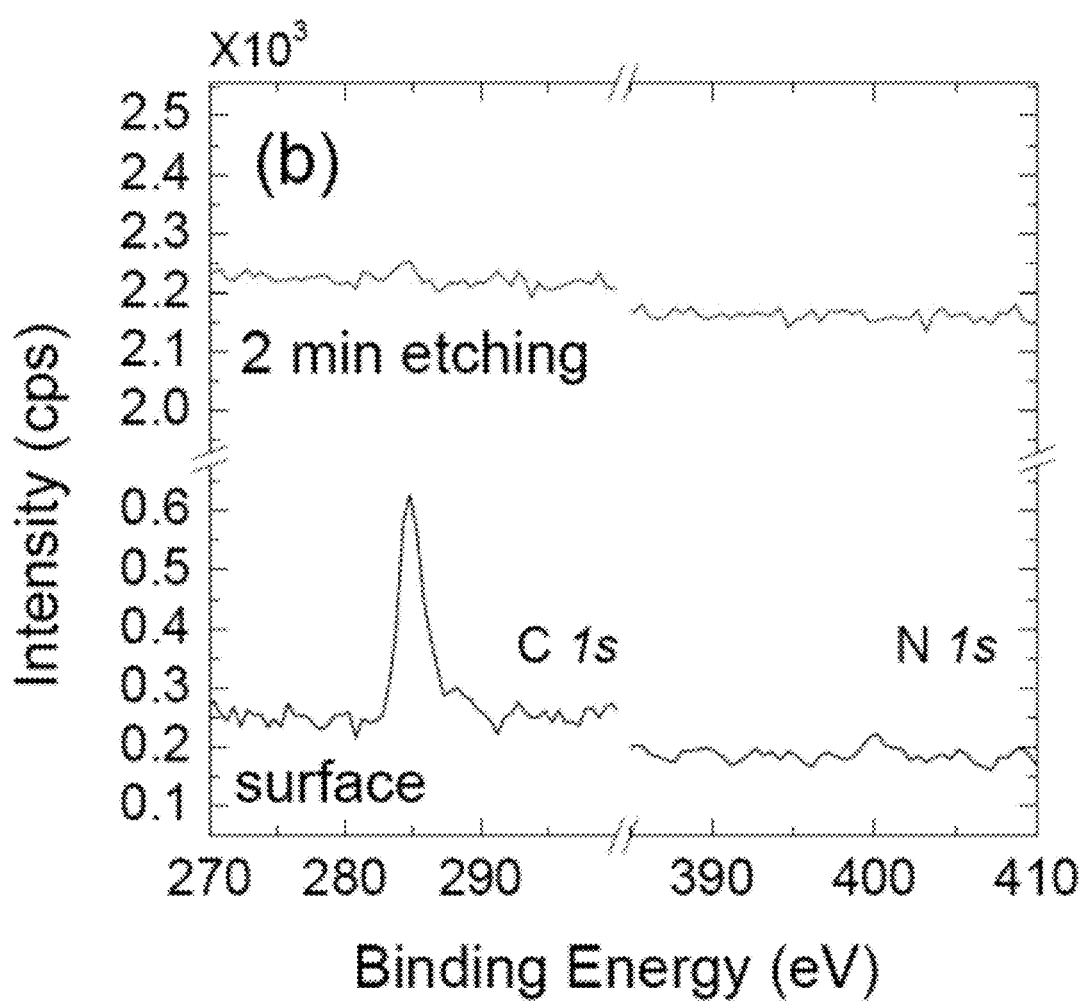
FIG. 8(b) shows a narrow scan XPS spectra for C1s and N1s peaks in accordance with certain embodiments.

Using a metal-organic precursor in vapor deposition can pose a possibility of impurity incorporation especially when the film grows at low temperature. Carbon and nitrogen from the ligands are typical examples of those impurities. XPS was used to look for impurities into the film. FIG. 8(a) shows the survey scan spectra of intact and 2 min-etched $SnO_2$ films deposited at 120° C. for three doses of both Sn precursor and $H_2O_2$. In this figure, all peaks except the two peaks at ~285 eV for C 1 s and at ~531 eV for O 1 s are attributed to Sn-related ones. that the C 1 s peak was observed in the surface spectrum, which might be due to incorporated carbon impurities or to surface contamination after air exposure. To find out the origin of the surface C 1 s peak, mild Ar sputtering for two minutes was carried out and the peak disappeared. The narrow scan spectra of the C 1 s and N 1 s peaks before and after the Ar sputtering are shown in FIG. 8(b). It is clearly seen in this figure that no C 1 s peak was observed after sputtering. This result shows that no carbon impurity is inside the film. In addition, N 1 s (~398 eV) narrow scan before and after 2-min Ar etching shows that the deposited $SnO_2$ film has no nitrogen, which might originate from residual ligands that had not been reacted with $H_2O_2$. This result together with RBS analysis clearly shows that this ALD process between the Sn precursor and $H_2O_2$ results in complete removal of the ligands. The quantitative analysis of the O/Sn ratio for as-deposited $SnO_x$ film surface without any sputtering yielded 1.76, which is lower than that (2.10) from the RBS measurement. This lower value may be due to an oxygen deficient surface layer.

Figure 9:
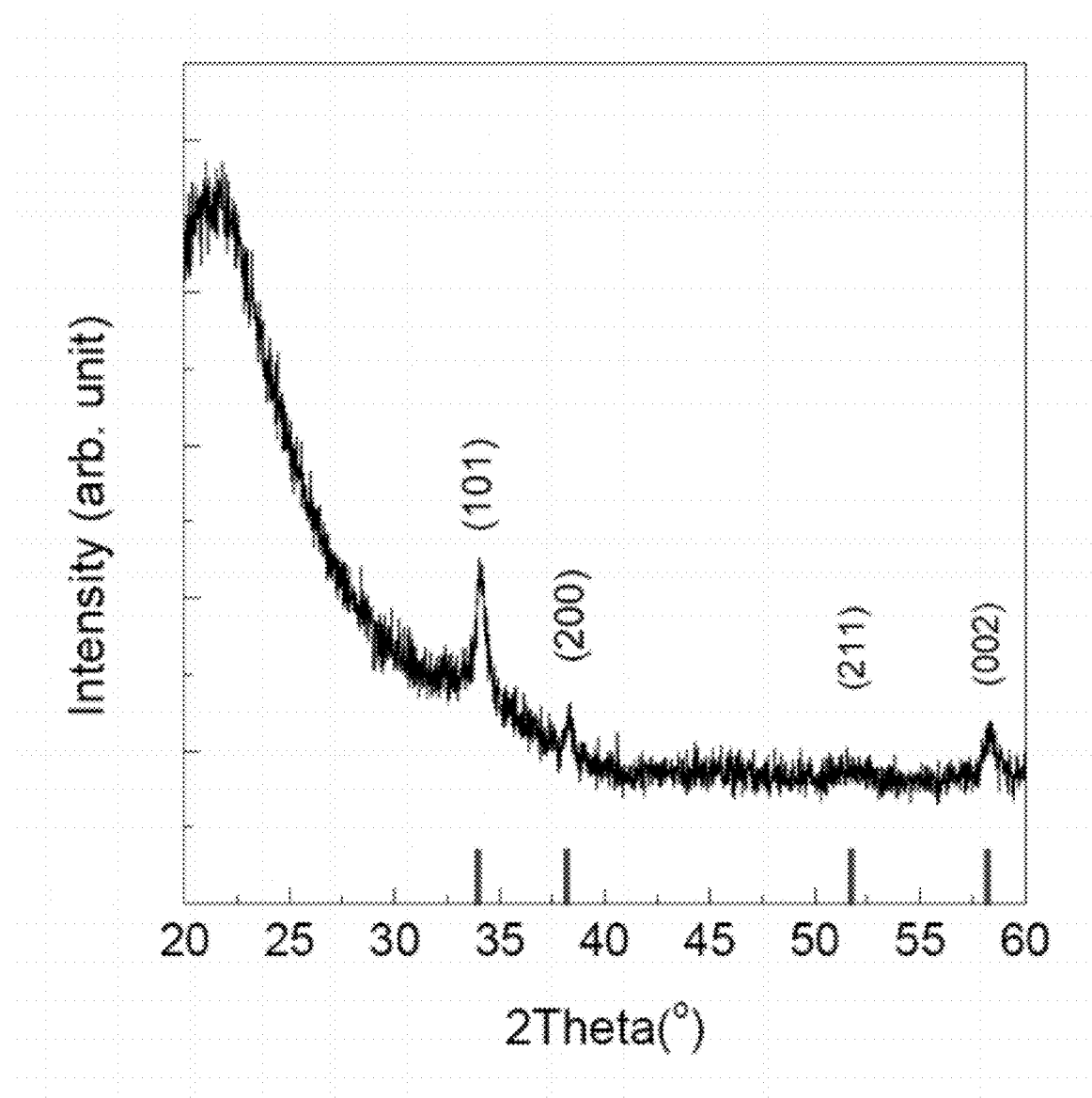
FIG. 9 shows an XRD pattern of a ~100 nm-thick $SnO_2$ film grown on a glass substrate, where the lines at the bottom of the figure indicate the location of each diffraction peak of the XRD pattern in accordance with certain embodiments.

FIG. 9 shows the X-ray diffraction pattern of a ~100 nm-thick $SnO_2$ film for three times injection of the Sn precursor and $H_2O_2$ on a glass substrate. It is seen from the figure that $SnO_2$ film deposited at 120° C. exhibits the crystalline structure of rutile $SnO_2$. The peaks at 34.1°, 38.3°, 51.6°, and 58.3° are assigned to (101), (200), (211), and (002) plane diffractions. The intense (110) peak reported to be at 26.6° was not observed in this figure, but interestingly it was observed in following selected area electron diffraction analysis.

Figure 10:
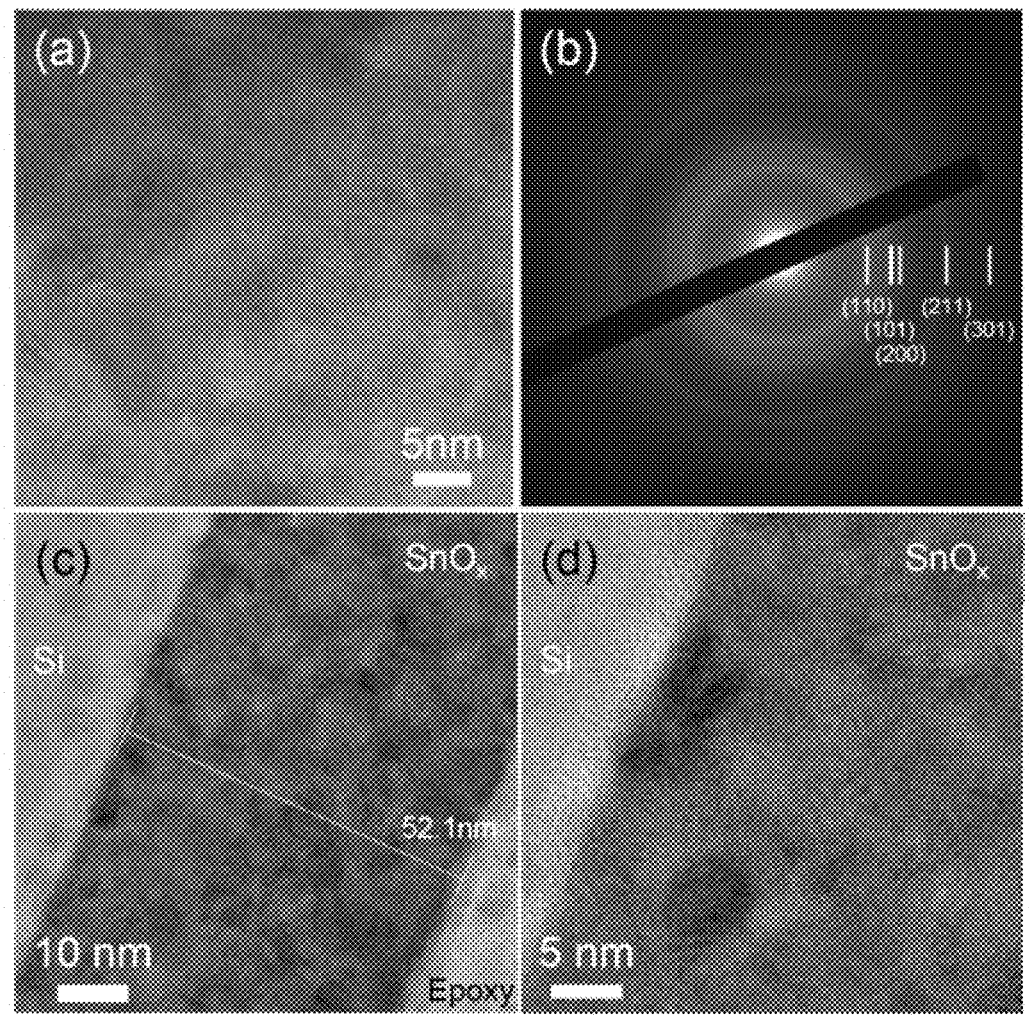
FIG. 10(a) shows a plan-view transmission electron microscopy image of a $SnO_2$ film on a 30 nm-thick SiN membrane in accordance with certain embodiments.
FIG. 10(b) shows a ring-shaped electron diffraction pattern from FIG. 10(a), where the diffraction rings are assigned to be (110), (101), (200), (211), and (301) plane diffractions in accordance with certain embodiments.
FIG. 10(c) shows a cross-section transmission electron microscopy image of a 52 nm-thick $SnO_2$ film on a Si substrate in accordance with certain embodiments.
FIG. 10(d) shows a cross-section high-resolution TEM image of nano-crystalline $SnO_2$ film, where a native oxide layer of ~2 nm is observed between a Si substrate and $SnO_2$ film in accordance with certain embodiments.

FIG. 10(a) shows the plan-view TEM image of ~35 nm-thick $SnO_2$ film (200 cycles) deposited on a 30 nm-thick SiN membrane. The as-deposited $SnO_2$ film on this thin membrane has a partially polycrystalline structure. A ring-shaped electron diffraction pattern of this film, as shown in FIG. 10(b), displays the polycrystalline nature of the deposited $SnO_2$ film, which was consistent with the XRD measurement. The diffraction rings are assigned to be (110), (101), (200), (211), and (301) diffractions, respectively. The formation of polycrystalline ALD-SnO$_2$ films at a low temperature of 120° C. has never been reported. FIG. 10(c) is a representative cross-section TEM image of the SnO$_2$ film for 300 cycles on a Si substrate. The film thickness of ~52 nm observed by TEM matched with the value from ellipsometry. Nano-crystalline structures in the SnO$_2$ film can be also identified in this figure. Similar structures were found on all substrates that were used. Many grain boundaries are also seen in this figure. From the high resolution image of FIG. 10(d) grain size of SnO$_2$ was estimated to be 5-10 nm. About 2 nm-thick native silicon oxide was also observed in this figure.

Figure 11:
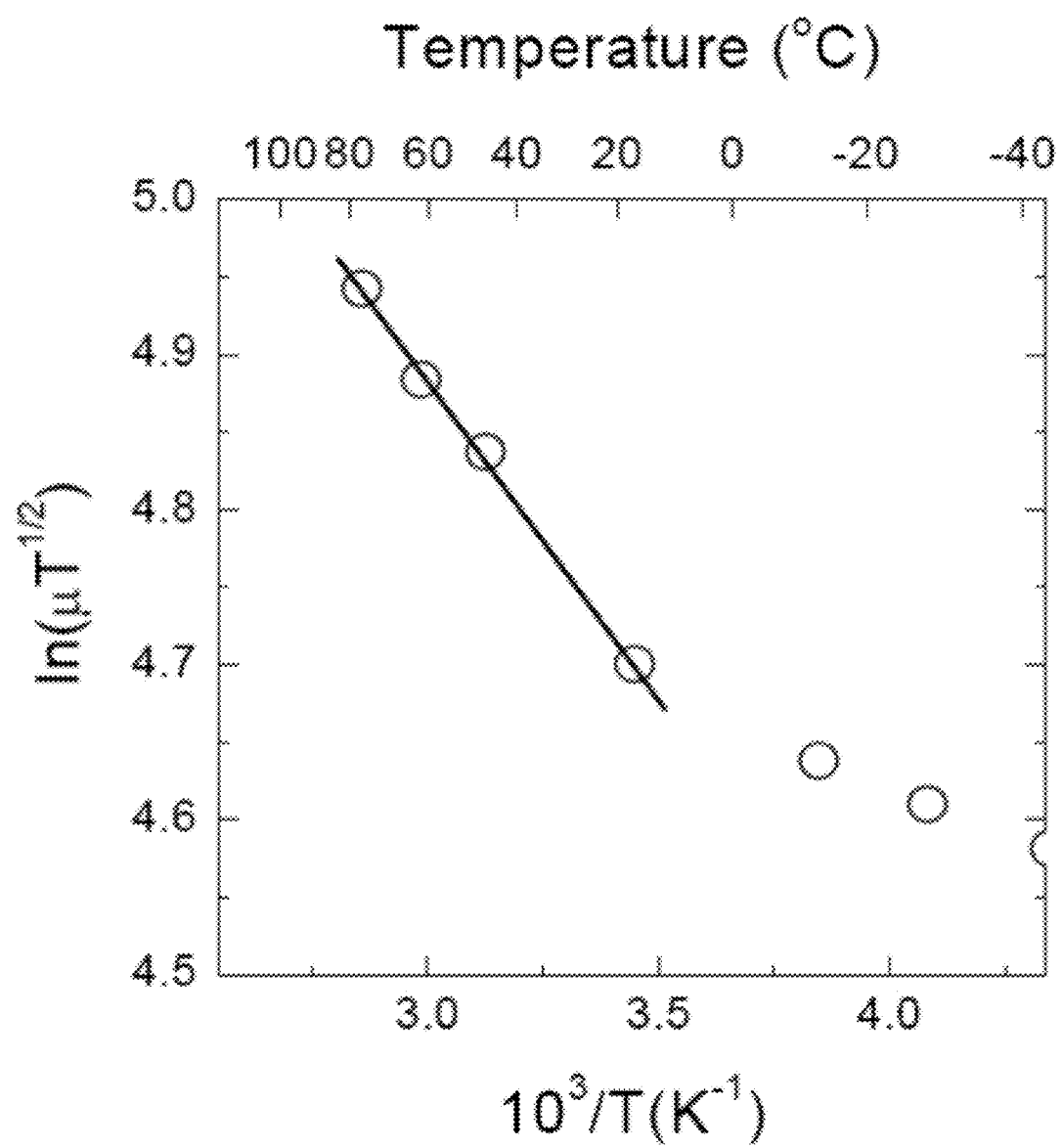
FIG. 11 shows the change in the mobility with the temperature as a plot of $\ln(\mu T^{1/2})$ vs. 1/T, where the straight line for high temperature region indicates that the mobility of the grown $SnO_2$ film is mainly limited by grain boundary scattering in accordance with certain embodiments.

FIG. 11 plots the mobility as a function of temperature. Here, 70 nm-thick SnO$_2$ from both three times injection of the Sn precursor and H$_2$O$_2$ was used. The three main scattering mechanisms limiting the observed mobility are optical phonon scattering, ionized impurity scattering, and grain boundary scattering. The mobility limited by grain boundary scattering is given by equation (1)

$$\mu = \mu_0 T^{-1/2} \exp\left(\frac{-\phi_b}{kT}\right) \quad (1)$$

where $\mu$ is mobility, $\mu_0$ is the pre-exponential term, T is temperature, and $\phi_b$ is potential barrier height. The plot of ln ($\mu T^{1/2}$) vs. 1/T of FIG. 11 gives a straight line at higher temperatures, which indicates that grain boundary scattering is the dominant mechanism in the as-deposited SnO$_2$ film. This may be due to the abundant grain boundaries of nano-crystalline grains of 5-10 nm size. The extracted grain boundary potential barrier ($\phi_b$) was 34 meV. When degenerate gas behavior was applied, the plot of ln($\mu$/T) vs. 1/T did not give any increase in $\mu$/T over the range 200-300 K. Also, no intentional doping into SnO$_2$ film was performed so that ionized scattering was less important than grain boundary scattering.

Figure 12:
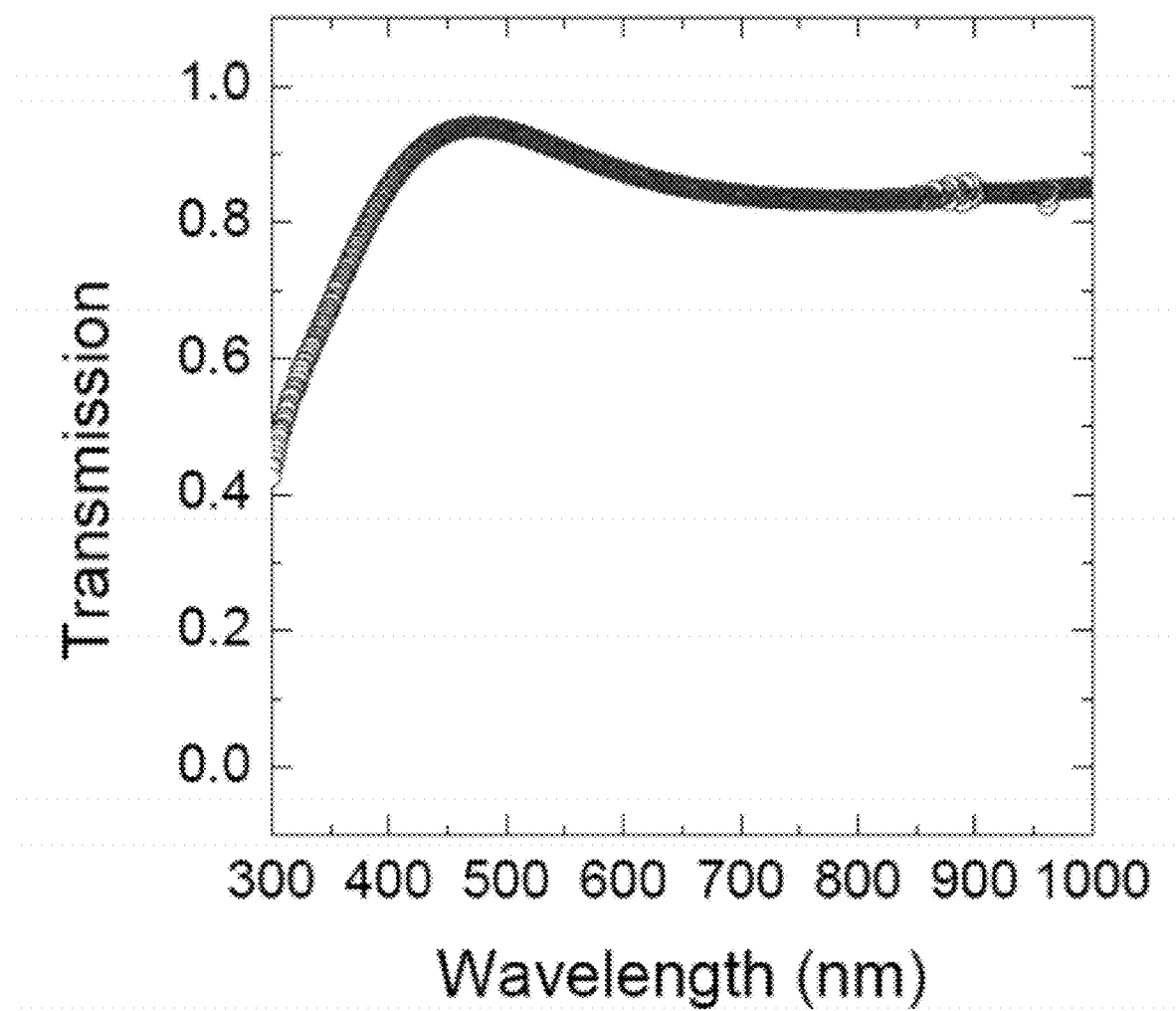
FIG. 12 shows a transmission spectrum for 100 nm-thick $SnO_2$ film on a quartz substrate in the wavelength from 400 to 1000 nm in accordance with certain embodiments.

FIG. 12 shows the optical transmission spectrum of an SnO$_2$ film measured by a UV-Vis spectrophotometer. Three times injection of both the Sn precursor and H$_2$O$_2$ was used and the film thickness was 100 nm. The background correction was done using an uncoated quartz substrate. The average transmission from 400 to 1000 nm wavelength was 87%. The average transparency is high enough to be used as a transparent electrode.

Figure 13:
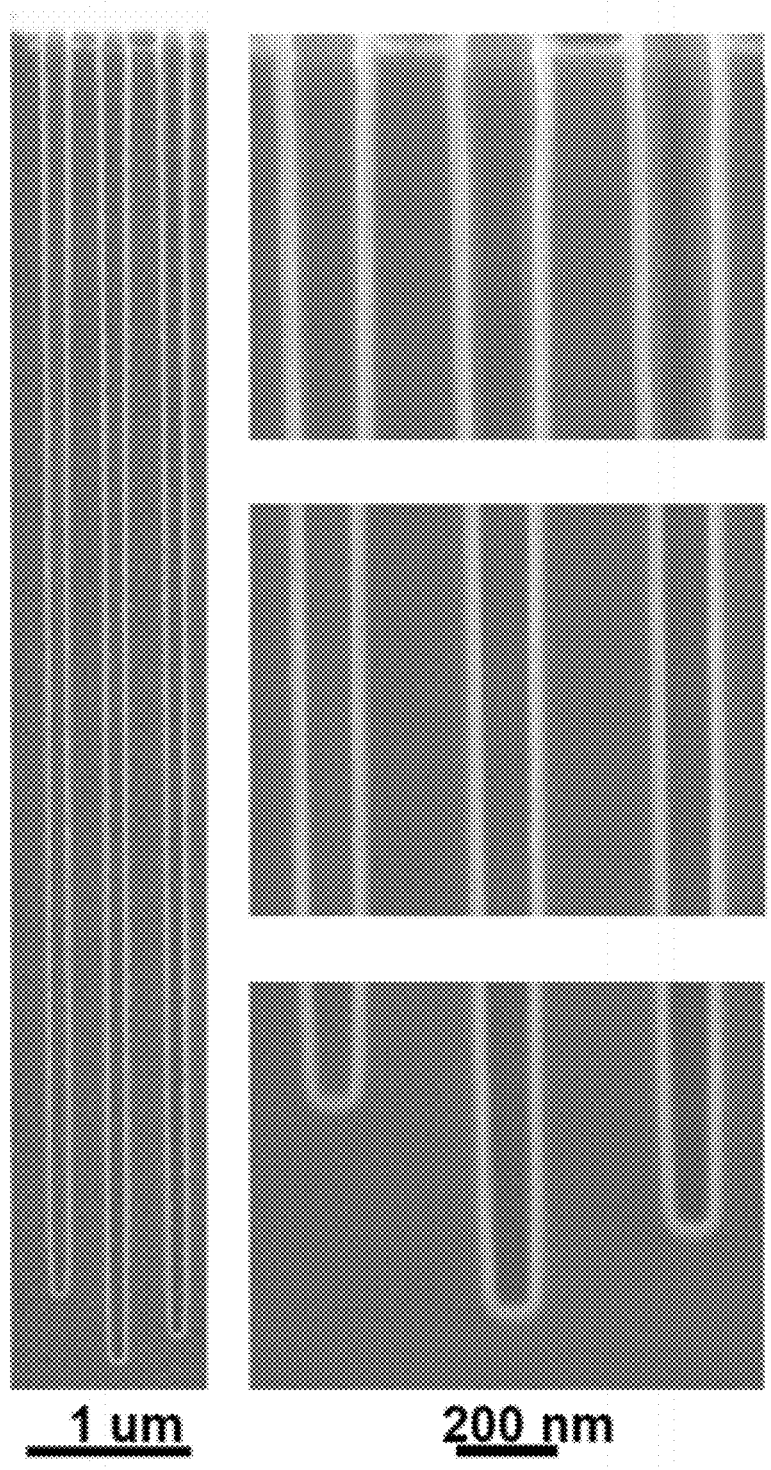
FIG. 13 shows a cross-sectional scanning electron micrograph of tin oxide film showing conformal coverage inside narrow trenches in accordance with certain embodiments.

A substrate with narrow holes (about 50:1 ratio of depth to diameter) was coated at 50° C. Examination of cleaved cross sections showed that ALD tin oxide coated the walls of the holes with >80% uniformity of thickness, as shown in FIG. 13.

In summary, a novel tin precursor was vaporized at 40° C. and the vapor pulsed into a vacuum chamber alternating with pulses of H$_2$O$_2$/H$_2$O from a liquid source at room temperature. Using this ALD process, films of conductive SnO$_2$ were obtained on substrates held at temperatures from 50° C. to 150° C. at a rate of around 0.18 nm/cycle. At substrate temperatures above 150° C. the deposition rate decreased. Thickness is linear in the number of cycles, with an induction period of not more than a few cycles. Successful growth was carried out on plastic substrates (epoxy and polyimide), metals (aluminum and stainless steel), oxides (silica, alumina and glass), and oxidized silicon and glassy carbon. Rutherford backscattering spectroscopy (RBS) and X-ray photoelectron spectroscopy (XPS) measurements showed that composition ratio of O/Sn is close to 2 and that the films do not contain any detectable carbon or nitrogen impurities. X-ray diffraction (XRD) and transmission electron microscopy (TEM) analyses identified crystallites with the rutile SnO$_2$ phase and average grain size of 5-10 nm. The density of the films is 83% of the bulk rutile phase. The surfaces are very smooth, with roughness about 2% of the film thickness. The average optical transmission is 87% for the wavelength from 400 to 1000 nm, and the refractive index is about 2. The films are conformal in holes with aspect ratios up to 50:1. The lowest resistivity is about 10$^{-2}$ ohm cm for material without intentional doping. The electron mobility is over 7 cm$^2$ V$^{-1}$ s$^{-1}$, and the free electron concentration reaches nearly 10$^{20}$ cm$^{-3}$. The dependence of mobility on temperature suggests that grain boundary scattering is the dominant scattering mechanism for the conduction electrons.

Example 2

No Deposition of Tin Oxide without any Oxygen Source

Example 2 was repeated using only the tin precursor, and no hydrogen peroxide vapor. No film was observed to have been deposited on the substrate surface. This result verifies that the film deposition in example 2 was due to the ALD reaction.

Example 3

Slow Deposition of Tin Oxide

Example 2 was repeated using only de-ionized water as an oxidant gas instead of 50 wt. % H$_2$O$_2$ while maintaining the other growth conditions. Under these conditions, a sharp decrease in the growth rate (to 0.016 nm/cycle) was observed. The difference in the growth rate between 50 wt. % H$_2$O$_2$ and water as oxidant gas was over ten times.

This result indicates that the higher growth rate with the use of 50% hydrogen peroxide as an oxidant gas resulted from the higher reactivity of the synthesized tin precursor to hydrogen peroxide than to water. This result further demonstrates that the growth kinetics of the tin oxide can be controlled as desired by controlling the relative ratio of hydrogen peroxide to water as desired.

Example 4

Tin Oxide from Nitrogen Dioxide as an Oxygen Source

Example 2 was repeated using nitrogen dioxide gas, NO$_2$, in place of hydrogen peroxide vapor. Electrically conductive and highly conformal tin oxide film was deposited on flat surfaces and conformally inside narrow holes with aspect ratio greater than 50:1. Similar results were obtained at substrate temperatures from 100 to 200° C.

Example 5

Synthesis of Tin Sulfide Films by ALD

Figure 14A:
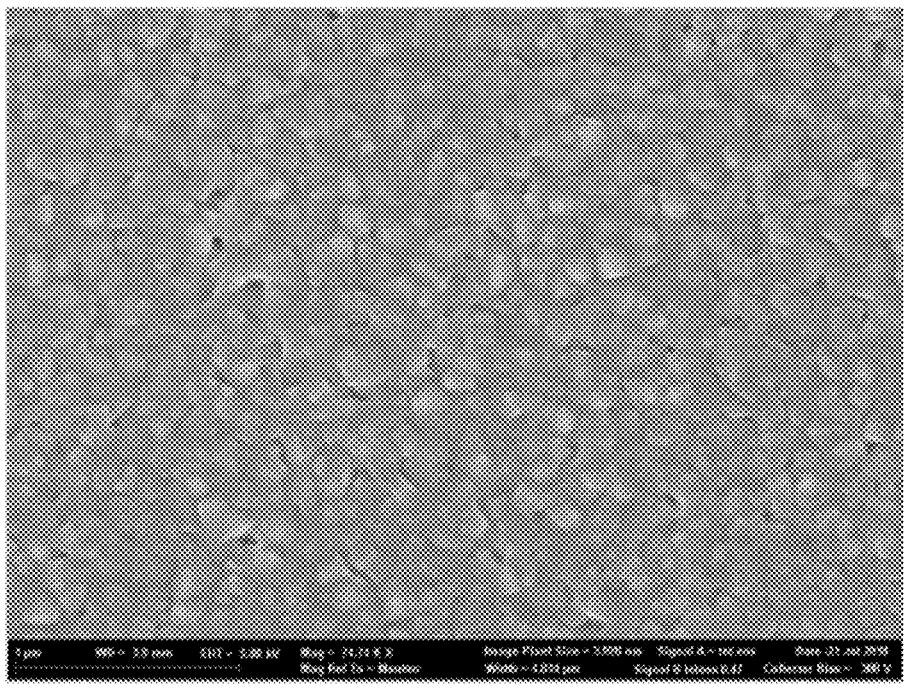
FIG. 14(a) shows a scanning electron microscope image of a top surface of a SnS film deposited in accordance with certain embodiments.
Figure 14B:
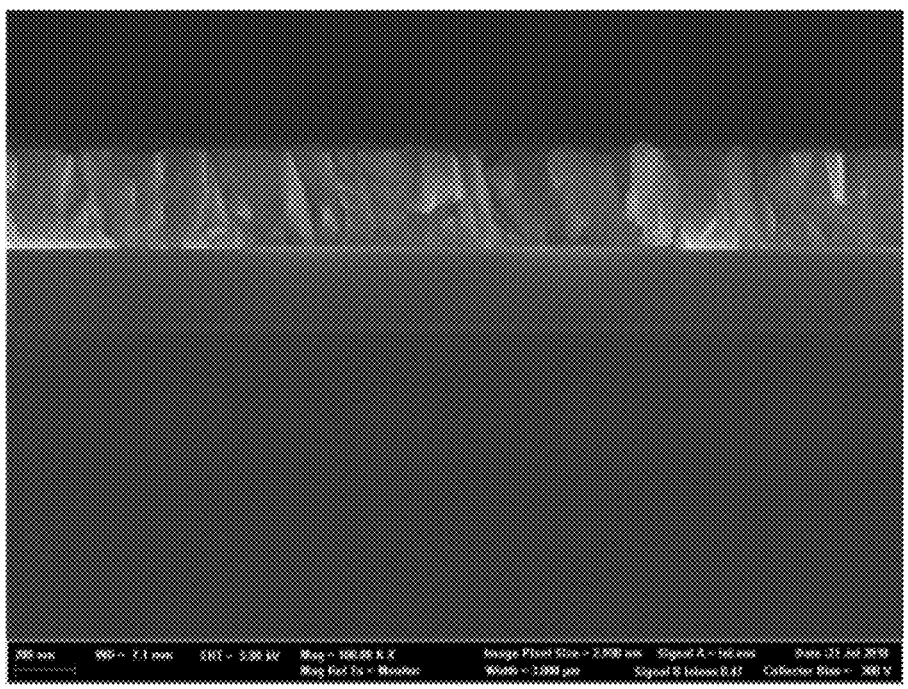
FIG. 14(b) shows a scanning electron microscope image of a cross section of a SnS film deposited in accordance with certain embodiments.

Example 2 was repeated, except that hydrogen sulfide gas was used in place of the hydrogen peroxide vapor. Conformal films of polycrystalline tin monosulfide, SnS, were deposited at substrate temperatures from 70 to 200° C. The growth per cycle was over 0.1 nm per cycle. FIG. 14 shows SEMs of (a) the top surface and (b) the cross section of a SnS film. The stoichiometry was confirmed to be SnS$_{1\pm0.01}$ by Rutherford Backscattering Spectroscopy. A film 188 nm thick showed an electrical sheet resistance of 2.4±0.4×10⁸ ohms per square. It is a p-type semiconductor with an optical band gap of 1.3 electron volts and very strong optical absorption in the visible (>10⁵ cm⁻¹) and near infrared (>10⁴ cm⁻¹) regions of the spectrum. The deposited films of SnS have potential application in solar photovoltaic cells.

Example 6

Synthesis of a Lead Precursor

Example 1 is repeated with PbCl₂ in place of SnCl₂. A lead precursor is obtained.

Similar processes can be used to deposit metal nitrides, metal selenides, metal phosphides, metal carbides, metal silicides, or metal borides using the tin or lead compounds of the present disclosure.

Materials produced according to the present disclosure may be used as components of displays, transparent transistors, light-emitting diodes, solar cells, electron multipliers and gas sensors.

Those skilled in the art will recognize or be able to ascertain many equivalents to the specific embodiments of the invention described specifically herein. Such equivalents are intended to be encompassed within the scope of the following claims.

What is claimed is:
1. A cyclic amide represented by the general formula

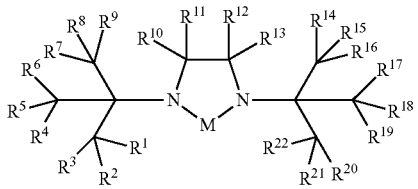

wherein M is tin or lead, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are selected independently from hydrogen, alkyl, cycloalkyl, alkenyl, alkynyl, trialkylsilyl, fluoroalkyl groups or alkyl groups substituted by other non-metal atoms or groups, and wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected to provide a cyclic amide capable of vaporizing prior to decomposition.

2. The cyclic amide of claim 1, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are each selected independently from the group of hydrogen and alkyl groups containing 1 to 4 carbon atoms.

3. The cyclic amide of claim 1, wherein $R^{10}$ and $R^{13}$ are methyl groups and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are hydrogen atoms, represented by the formula

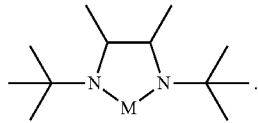

4. The cyclic amide of claim 3, wherein M is tin.
5. The cyclic amide of claim 3, wherein M is lead.
6. The cyclic amide of claim 1, wherein M is tin.
7. The cyclic amide of claim 1, wherein M is lead.
8. A process comprising depositing the cyclic amide of claim 1 to form a solid material comprising tin or lead.
9. The process of claim 8, further comprising alternately depositing a second reactant after each deposition of the cyclic amide of claim 1.
10. The process of claim 8, wherein the cyclic amide of claim 1 is deposited with a second reactant.
11. The process of claim 8, wherein the solid material is a metal.
12. The process of claim 8, wherein the solid material is a metal oxide.
13. The process of claim 8, wherein the solid material is a metal sulfide.
14. The process of claim 8, wherein the solid material is a metal selenide.
15. The process of claim 8, wherein the solid material is a metal nitride.
16. The process of claim 8, wherein the solid material is a metal phosphide.
17. The process of claim 8, wherein the solid material is a metal carbide.
18. The process of claim 8, wherein the solid material is a metal silicide.
19. The process of claim 8, wherein the solid material is a metal boride.
20. The process of claim 8, wherein the solid material is a component of a transistor device.
21. The process of claim 8, wherein the solid material is a component of a display device.
22. The process of claim 8, wherein the solid material is a component of a solar cell.

* * * * *